(12) United States Patent
Homma

(10) Patent No.: US 7,585,274 B2
(45) Date of Patent: Sep. 8, 2009

(54) OPTICAL SYSTEM FOR ENDOSCOPES

(75) Inventor: Hiroyuki Homma, Sagamihara (JP)

(73) Assignee: Olympus Corporation, Tokyo (JP)

( * ) Notice: Subject to any disclaimer, the term of this patent is extended or adjusted under 35 U.S.C. 154(b) by 658 days.

(21) Appl. No.: 11/213,905

(22) Filed: Aug. 30, 2005

(65) Prior Publication Data

US 2006/0052668 A1  Mar. 9, 2006

(30) Foreign Application Priority Data

Sep. 3, 2004   (JP) .............................. 2004-256904

(51) Int. Cl.
*A61B 1/06* (2006.01)
(52) U.S. Cl. .................. 600/160; 600/177; 600/176
(58) Field of Classification Search ................ 600/101, 600/129, 160, 176–180, 182; 362/572, 574; 385/117, 119; 607/93; 359/433
See application file for complete search history.

(56) References Cited

U.S. PATENT DOCUMENTS

| 4,111,561 | A  | * | 9/1978  | Plummer ..................... 356/225 |
| 4,415,240 | A  | * | 11/1983 | Nishioka et al. .............. 385/33 |
| 6,053,862 | A  | * | 4/2000  | Ono ............................ 600/177 |
| 6,251,068 | B1 | * | 6/2001  | Akiba et al. ................ 600/182 |
| 6,735,367 | B2 | * | 5/2004  | Sanso ......................... 385/117 |
| 2001/0031115 | A1 | * | 10/2001 | Chen et al. ..................... 385/54 |
| 2002/0076180 | A1 | * | 6/2002  | Miyano ....................... 385/117 |
| 2005/0124858 | A1 | * | 6/2005  | Matsuzawa et al. .......... 600/176 |

FOREIGN PATENT DOCUMENTS

| JP | 05-157967  | 6/1993 |
| JP | 06-148519  | 5/1994 |
| JP | 10-239586  | 9/1998 |
| JP | 2001-166223 | 6/2001 |
| JP | 2002-182126 | 6/2002 |

* cited by examiner

*Primary Examiner*—John P Leubecker
*Assistant Examiner*—Samuel Candler
(74) *Attorney, Agent, or Firm*—Kenyon & Kenyon LLP

(57) ABSTRACT

An optical system for an endoscope can be used by being disposed in the distal end portion of the endoscope, the optical system having a plurality of illumination optical systems, which allow light emitted from a light source to diverge, and an observation optical system, in which at least one of the plurality of illumination optical systems satisfies the following formula (1):

$$0 \leq -df(\theta)/d\theta \leq 0.025, 10° \leq \theta \leq 85° \qquad (1),$$

wherein $\theta$ denotes an angle of emission from a center of the illumination optical system, and $f(\theta)$ denotes a value obtained by standardizing, at an illuminance at a time when the angle $\theta$ of emission is 0°, an illuminance distribution (spherical light distribution characteristics) at a time when a spherical object is illuminated by the illumination optical system.

8 Claims, 22 Drawing Sheets

SPHERICAL LIGHT DISTRIBUTION
(DISTANCE OF 40 mm TO OBJECT SURFACE)

OPTICAL SYSTEM FOR ENDOSCOPES

CROSS-REFERENCE TO RELATED APPLICATIONS

This application claims benefit under 35 U.S.C. §119 of Japanese Patent Application No. 2004-256,904, filed in Japan on Sep. 3, 2004, the contents of which are hereby incorporated by reference.

BACKGROUND OF THE INVENTION

1. Field of the Invention

This invention relates to an optical system for an endoscope, particularly to an optical system for use in the distal end of the endoscope.

2. Description of the Related Art

Since the inside of a body cavity when it is the observation object of a medical endoscope is dark, the inside needs to be illuminated, when it is observed. To perform the illumination using an endoscope, light exiting from a light source is generally guided to a distal end portion of the endoscope by a light guide fiber bundle disposed in the endoscope, and an observation object in the body cavity is illuminated via an illumination optical system disposed in the distal end portion to illuminate a visual field area.

If a broad area can be observed at the same time with the endoscope, the medical check-up time can be reduced to reduce a patient's burden. Therefore, the field angle of an observation optical system in an endoscope is generally set to be broad. Moreover, the illumination system (light guide fiber bundle, illumination optical system, etc.) is disposed in such a manner that the broad area can be brightly illuminated in accordance with the large field angle of the observation optical system.

Specifically, first, a light guide fiber bundle having a large numerical aperture (NA), for example, an NA of 0.6 or more is selected as the light guide fiber bundle for the endoscope, and a light beam having a large light distribution angle is guided to the distal end portion of the endoscope with a high light transmission efficiency by use of this light guide fiber bundle. Moreover, the light distribution angle is further broadened by the illumination optical system disposed in the distal end portion of the endoscope, so that the visual field area of the observation optical system can be well illuminated.

In recent years, there has been a demand for an endoscope having a larger field angle. To meet the demand, an observation optical system having a larger field angle needs to be disposed in the distal end portion of the endoscope. Moreover, the illumination optical system is required to have a large enough light distribution angle so as to be capable of sufficiently illuminating the broader visual field area of the observation optical system.

FIG. 27 is a diagram showing one example of a conventional illumination optical system for an endoscope. This illumination optical system is made up of a negative lens 2 disposed in front of an emission end surface of a light guide fiber bundle 1, and the whole visual field of the observation optical system (not shown) can be illuminated with the light emitted from the light guide fiber bundle 1. In this illumination optical system, the curvature of a concave surface of the negative lens 2 needs to be increased in order to broaden the light distribution angle. However, in this illumination optical system, the light emitted from the light guide fiber bundle 1 is outwardly refracted. Therefore, the outer diameter of the negative lens 2 needs to be increased in order to prevent the light from being eclipsed in the periphery of the negative lens 2. Accordingly, there is a need to increase the outer diameter of the distal end portion of the endoscope. Therefore, the increasing of the curvature of the concave surface of the negative lens 2 goes against a demand for the reduction of the diameter of the endoscope, and is not realistic.

FIG. 28 is a diagram showing another example of a conventional illumination optical system for an endoscope. This illumination optical system is described in Laid-Open Japanese Patent Application No. 10-239586, and can satisfy the demand for the reduction of the diameter of the endoscope.

The illumination optical system shown in FIG. 28 comprises a plano-convex lens 3 disposed in front of the emission end surface of the light guide fiber bundle 1 and having a positive power. The illumination optical system for the endoscope brings the light emitted from the light guide fiber bundle 1 into convergence, and then allows the light to diverge. Therefore, it is possible to reduce the outer diameter of the lens in the illumination optical system as compared with the illumination optical system using the negative lens 2 shown in FIG. 27.

Additionally, the light guide fiber bundle 1 is formed by bundling a plurality of fibers. As shown in FIG. 29A, only core portions C of each fiber transmit the light. Therefore, in the emission end surface of the light guide fiber bundle 1, only the core portions arranged in a dot-matrix form emit the light. As shown in FIG. 29B, the illumination optical system having a positive power projects the emission end surface of the light guide fiber bundle 1 onto an object surface 4 in a magnified manner. Therefore, as shown in FIG. 29C, the illumination light projected onto the object surface 4 causes a dot-matrix-like illuminance unevenness (non-uniformity of illuminance).

To solve this problem, an illumination optical system is described in Laid-Open Japanese Patent Application No. 5-157967 or 6-148519 in which a single fiber rod is inserted between the light guide fiber bundle 1 and a positive lens to prevent the dot-matrix-like illuminance unevenness from being generated. FIG. 36 is a diagram showing one of the described examples.

In the illumination optical system shown in FIG. 36, the length of a single fiber rod 5 needs to be sufficiently increased in order to obtain from only the single fiber rod 5 a sufficient light diffusing effect for preventing the generation of the dot-matrix-like illuminance unevenness. However, when the single fiber rod 5 is lengthened, the total length of the illumination optical system 6 increases, and this cannot satisfy a demand for the reduction of the total length of the optical system in the endoscope.

FIG. 30 is a diagram showing another example of a conventional illumination optical system for an endoscope. This illumination optical system for an endoscope is described in Laid-Open Japanese Patent Application No. 2002-182126.

In the illumination optical system 5, the single fiber rod is used as the material of a third lens 53 in order to eliminate the dot-matrix-like illuminance unevenness, and the curvature is imparted to one surface of each lens. Since three lenses are included, the total length of the optical system necessarily increases.

The above-described illumination optical system is usually used in combination with an observation optical system having a field angle of 120° to 140°, but when the illumination optical system is used in combination with the observation optical system having a field angle of 150° or more, there occurs a disadvantage in that the visual field periphery (vicinity of an inner edge of an observable area (visual field)) of the observation optical system darkens, and cannot practically be observed.

This aspect will be described hereinafter from two viewpoints: light distribution characteristics of the illumination optical system; and a positional relation between the observation optical system and the illumination optical system.

First, the light distribution characteristics of the illumination optical system will be described.

An inner surface of the stomach or large intestine, which is an object of a medical endoscope, can be regarded as a schematically spherical surface or an inner surface of an empty tube. In these two surfaces, the spherical object surface is more difficult to be brightly illuminated in a broader area than the inner surface of the empty tube. Therefore, the illumination optical system that exhibits satisfactory light distribution characteristics when evaluated under conditions where a spherical object is illuminated, also exhibited a satisfactory light distribution characteristics, when used for illuminating another object.

In an endoscope having a field angle of 140° or less, the illumination optical system preferably has such spherical light distribution characteristics (illuminance distribution of the illumination light on the spherical object surface) as to be as flat as possible from a center of the visual field to the periphery and to reduce the illuminance unevenness.

FIG. 31 is a diagram showing one example of the spherical light distribution characteristics of the negative lens shown in FIG. 27. It is seen that the amount of a change of the illuminance is small up to an emission angle of 40°, but the change amount of the illuminance increases, when the angle of emission exceeds 50°. The angle of emission at which the change of the illuminance increases corresponds to a peripheral portion of the visual field on the object surface. Therefore, one feels that the periphery of the visual field is dark as compared with the vicinity of the center. The illumination optical system having such spherical light distribution characteristics has practicability as an illumination optical system which illuminates the visual field of an observation optical system having a field angle of 100°. However, it can be confirmed through experiments that one feels that the illumination optical system is unsuitably dark for the system which illuminates the visual field of the observation optical system whose angle of field exceeds 100°. When the curvature of a curved surface of this negative lens is increased, the light diverges more intensely. Therefore, the light distribution angle of the illumination optical system broadens, and it is possible to increase the angle of emission at which the change of the illuminance increases. However, the outer diameter of the negative lens increases as described above. This illumination system empirically bears a practical use in an endoscope whose angle of field is 120° or less. When this angle is exceeded, the visual field periphery cannot be observed.

Next, FIG. 33 shows the spherical light distribution characteristics of an illumination optical system made up of three positive lenses shown in FIG. 30. In the figure, notation "example" indicates that the corresponding curve shows the characteristics of the example of this prior-art document. The light guide fiber bundle has an NA of 0.76. The illumination optical system retains a high illuminance at an emission angle of about 50°. Therefore, when the system is used in an endoscope having a field angle of about 120°, the brightness is sufficient up to the visual field periphery, and a flat light distribution is obtained up to the visual field periphery. However, when the angle of emission exceeds 55°, the illuminance rapidly drops, and darkness becomes conspicuous. Therefore, although the illumination system has a high absolute illuminance, it is unsuitable in a system for illuminating the visual field of an observation optical system having a field angle of 150° or more, since the change of the illuminance is large, thereby giving an impression that the visual field periphery is dark. Supposing that it is possible to realize an illumination optical system having a high illuminance up to an emission angle of 70°, an area of a field angle of 150° is sufficiently brightly illuminated. However, when the system has the above-described light distribution characteristics, even a non-observed area outside the visual field area is illuminated, and this is not desirable with regard to illumination efficiency.

To realize a wide-angle illumination system, the change of the illuminance is comparatively moderate, and the absolute illuminance needs to have a value which is not less than a certain value in the visual field periphery, but the above-described illumination optical system does not satisfy this requirement.

Next, the positional relation between the observation optical system and the illumination optical system will be described. When a distal end surface of the endoscope comes within 10 mm or closer to the object, the light distribution in the visual field of the observation optical system largely depends on not only the light distribution characteristics of the illumination optical system but also on the positional relation between the observation optical system and each illumination system. FIG. 34 is a diagram showing a positional relation between the illumination optical system and the observation optical system, and that between an area illuminated by the illumination optical system and the visual field of the observation optical system. In the figure, reference numeral 10 denotes an illumination optical system, 9 denotes an observation optical system, an area 11 where slant lines are drawn denotes an area illuminated by the illumination optical system 10, and 12 denotes a visual field of the observation optical system. In the case where the distal end surface of the endoscope comes close to the object, when the observation optical system is apart from the illumination optical system, as shown in FIG. 34, there are problems in that the area 11 illuminated by the illumination optical system 10 does not cover the whole visual field 12 of the observation optical system 9, and that a portion which is not included in a slant line portion in the visual field 12 is not bright. The conventional illumination optical system for an endoscope which is to improve the problems is described in Laid-Open Japanese Patent Application No. 2001-166223.

FIG. 35 is a diagram showing a layout of the observation optical system and the illumination optical system in the endoscope described in the Laid-Open Japanese Patent Application No. 2001-166223. This endoscope is provided with four illumination optical systems around the observation optical system 9, and the four illumination optical systems include two types of illumination optical systems 101 and 102 having different quantities of emitted light. The Laid-Open Japanese Patent Application No. 2001-166223, describes that, by use of this arrangement, a balance of the light distribution is improved in the case where the distal end surface of the endoscope comes close to the object.

However, it is difficult to improve the balance of the light distribution at the time when the distal end surface of the endoscope comes close to the object up to a sufficiently satisfactory level of wide-angle illumination only by the positional relation between the observation optical system and the illumination optical system and the quantity of emitted light. That is, when the improvement of the balance of the light distribution is considered, the light distribution characteristics inherent in the illumination optical system need to be sufficiently considered.

BRIEF SUMMARY OF THE INVENTION

According to one aspect of the present invention, there is provided an endoscope optical system disposed in a distal end portion of an endoscope, and having a plurality of illumination optical systems which allow light emitted from a light source to diverge and an observation optical system, wherein at least one of the plurality of illumination optical systems satisfies the following condition (1):

$$0 \leq -df(\theta)/d\theta < 0.025, 10° \leq \theta \leq 85° \quad (1),$$

wherein θ denotes an angle of emission of the light ray emitted from the center of the illumination optical system, which enters the illumination optical system in parallel with its optical axis, and f(θ) denotes a spherical light distribution characteristics, that is, an illuminance distribution at a time when a spherical object is illuminated by the illumination optical system. This illuminance distribution f(θ) indicates a relative value assuming that the illuminance at a time when the angle θ of emission is 0° is 1.

Other characteristics and advantages of the present invention will be apparent according to embodiments described hereinafter and appended claims.

BRIEF DESCRIPTION OF THE DRAWINGS

FIG. 16A is a diagram of a layout of the endoscope optical system as viewed from an object side, and FIG. 16B is a diagram showing a part of a section along line 16B-16B of FIG. 16A;

DETAILED DESCRIPTION

As described above, an endoscope optical system of the present invention is disposed in the distal end portion of an endoscope, and has a plurality of illumination optical systems which allow light emitted from a light source to diverge, and an observation optical system, and at least one of the plurality of illumination optical systems satisfies the following condition (1):

$$0 \leq -df(\theta)/d\theta < 0.025,\ 10° \leq \theta \leq 85° \qquad (1),$$

wherein θ denotes an angle of emission of the light ray emitted from the center of the illumination optical system, which enters the illumination optical system in parallel with its optical axis, and f(θ) denotes spherical light distribution characteristics, that is, an illuminance distribution at a time when a spherical object is illuminated by the illumination optical system. This illuminance distribution f(θ) indicates a relative value assuming that an illuminance at a time when the angle θ of emission is 0° is 1.

According to this arrangement, it is possible to obtain an endoscope optical system provided with an illumination optical system which is usable in an endoscope having a large angle of field and which can illuminate a spherical object disposed at a distant position without bringing darkness up to the visual field periphery.

Figure 25:
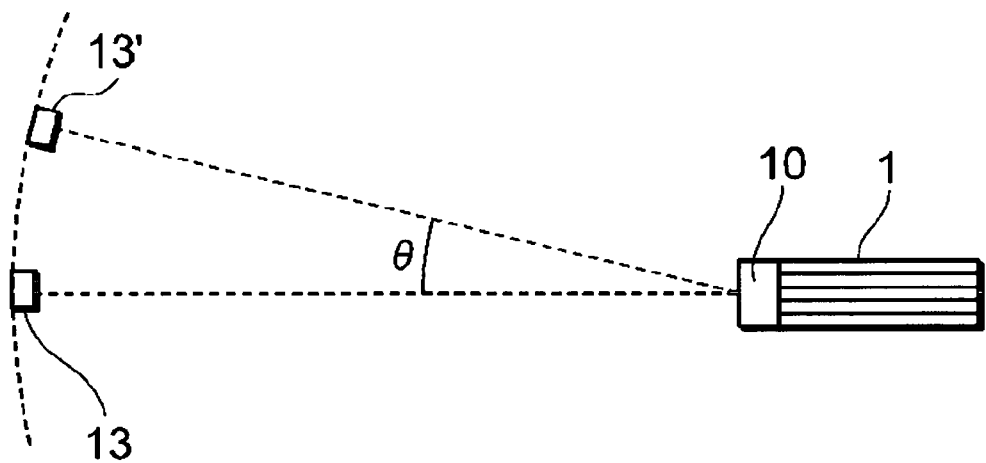
FIG. 25 is an explanatory view of the spherical light distribution characteristics f(θ)

The symbol f(θ) denotes the spherical light distribution characteristics. In FIG. 25, reference numerals 13 and 13' indicate two positions on the surface of the spherical object disposed at a position distant from an illumination optical system 10. The position 13 exists on an extended line of a centerline of the illumination optical system 10, and 13' exists on a line which is oblique by an angle θ from the centerline. Assuming that the illuminance of the position 13 at a time when the spherical object is illuminated by the illumination optical system is A, and the illuminance of the position 13' is B, f(θ)=B/A. That is, f(θ) is a relative illuminance value at a time when the illuminance at an emission angle θ=0° is 1.

Figure 37:
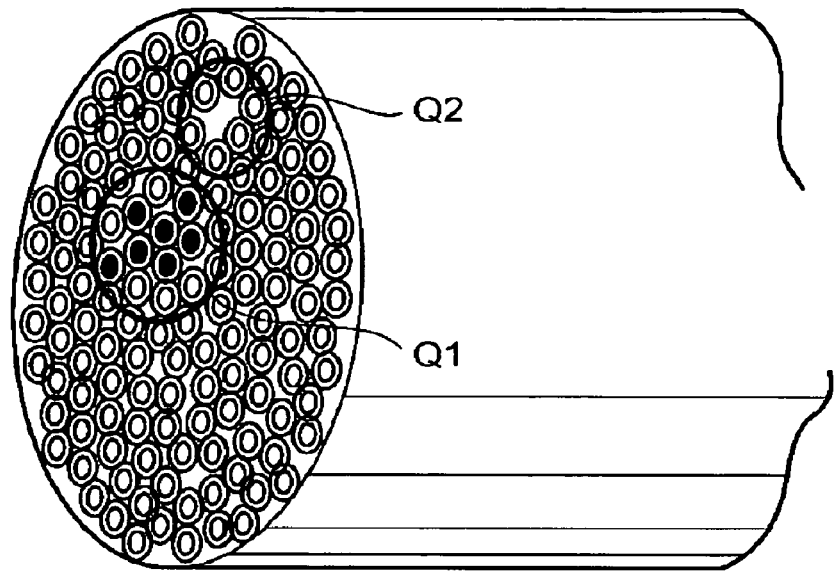
FIG. 37 is a diagram showing broken fibers or deviating fibers appearing in an end surface of the light guide fiber bundle.
Figure 38:
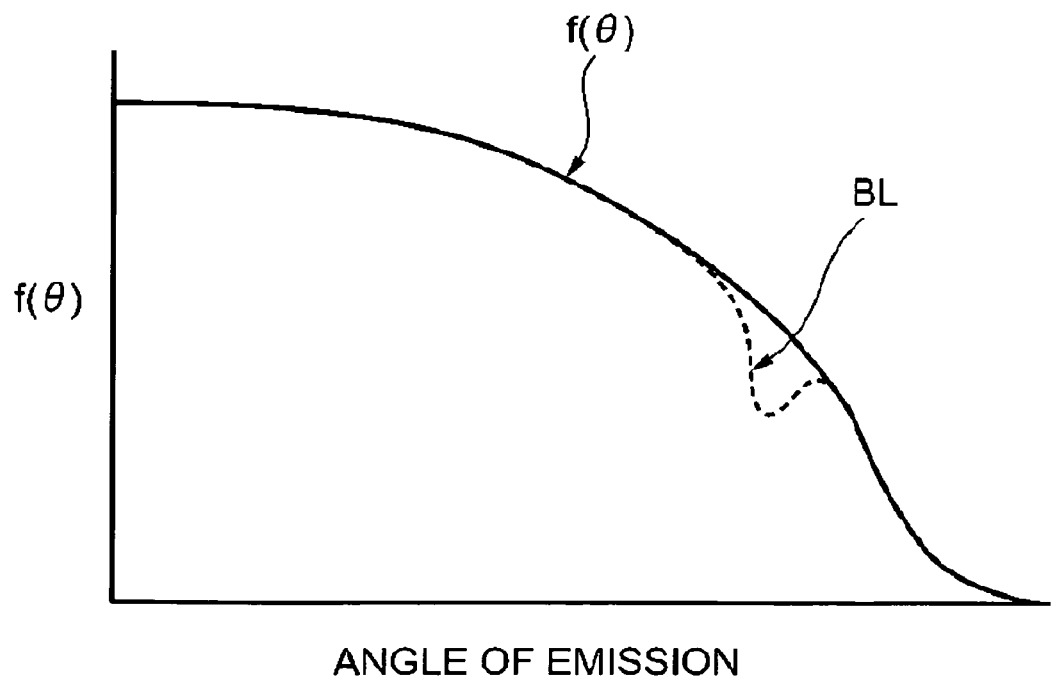
FIG. 38 is a diagram showing extraordinary fluctuations of the light distribution characteristics caused by the broken or deviating fibers appearing in the end surface of the light guide fiber bundle.

It is to be noted that when the endoscope is assembled, or is being used, fibers which constitute the light guide fiber bundle are sometimes broken. When a large number of fibers are bundled in the process of making the fiber bundle, the fibers sometimes deviate. Therefore, when the end surface of the light guide fiber bundle is observed, as shown in FIG. 37, there can exist a portion in which a part of fibers does not emit any light (area shown by a circle Q1) or a portion in which a density of the fibers is not uniform (area shown by a circle Q2). Therefore, in an actual illuminance distribution, as shown by a broken line in FIG. 38, a extraordinary unevenness is sometimes generated, that is, a portion BL which darkens due to extraordinary drops of the light distribution characteristics. The spherical light distribution characteristics f(θ) are light distribution characteristics in which a extraordinary illuminance change due to the breaking or deviating of the light guide fiber bundle is ignored.

Here, the condition (1) gives a condition, in the range of emission angle θ 10° to 85°, to make the illumination optical system have a light distribution whose illuminance on the spherical object surface is less dependent on the emission angle and any darkness is not felt up to the periphery in the illumination field. When −df(θ)/dθ exceeds the upper limit value of the condition (1) and increases, the change of the illuminance becomes large, and an impression of darkness is easily given. In actuality, when −df(θ)/dθ exceeds 0.025, one feels that the periphery is dark. It is to be noted that when the upper limit value of the condition (1) is set to 0.02 or less, it is preferably possible to increase the effect of preventing the feeling that the periphery is dark.

By use of an illumination optical system which satisfies the condition (1) in an endoscope having a field angle of 150° or more, it is possible to realize an endoscope optical system which is bright from the center of the visual field to the periphery. When a plurality of illumination optical systems are combined, the light distribution characteristics can be more easily controlled.

The illumination optical system which satisfies the condition (1) more preferably satisfies the following condition (2):

$$0 \leq -df(\theta)/d\theta < 0.02,\ 65° \leq \theta \leq 80° \qquad (2).$$

An absolute illuminance in a visual field peripheral portion of the object surface observed by the observation optical system having a half field angle of 65° or more is small as compared with that of the central portion of the visual field. Therefore, when the illuminance change is large, the darkness is more easily noticed. To solve the problem, when the change of the illuminance at an emission angle of 65° to 80° is set to 0.02 or less, the darkness cannot be easily noticed. When this change is set to 0.015 or less, the system becomes more effective.

Moreover, in a case where:

the endoscope optical system has three illumination optical systems;

the three illumination optical systems are arranged in such a manner that the center of a lens closest to the object side of the observation optical system is positioned in a triangle made by mutually connecting centers of lenses closest to the object sides of the three illumination optical systems; and assuming that a direction of a straight line connecting the center of the lens closest to the object side of the observation optical system to that of the lens closest to the object side of one illumination optical system is 0°, and angles in directions of straight lines connecting the center of the lens closest to the object side of the observation optical system to the centers of the lenses closest to the object sides of the other two illumination optical systems are $\phi 1$, $\phi 2$, respectively, the following formulas (3), (4) are preferably satisfied:

$$95° \leq \phi 1 \leq 145° \quad (3); \text{ and}$$

$$215° \leq \phi 2 \leq 265° \quad (4).$$

Furthermore, assuming that the distance from the center of the lens closest to the object side of the observation optical system to that of the lens closest to the object side of each illumination optical system is r, the following condition (5) is preferably satisfied:

$$1.3 \leq r/d \leq 3 \quad (5);$$

wherein d denotes an outer diameter of the lens closest to the object side in the observation optical system.

Here, each of $\phi 1$, $\phi 2$ can take three different values in accordance with the above-described "one illumination optical system" selected from the three illumination optical systems. At least one of these values may satisfy the above-described conditions (3) and (4).

When the distal end surface of the endoscope comes within about 10 mm from the object, the light distribution characteristics largely depend on a positional relation between the observation optical system and the respective illumination optical systems. When three illumination optical systems are arranged in such a manner as to surround the observation optical system, it is possible to reduce the illuminance unevenness at a time when the distal end surface of the endoscope is brought close to the object. Furthermore, when the illumination optical system is symmetrically disposed in such a position as to satisfy the above-described formulas (3) and (4), it is possible to perform optimization for reducing the illuminance unevenness at the time when the distal end surface of the endoscope is brought close to the object. Unless the conditions are satisfied, the illuminance unevenness at the time when the distal end surface of the endoscope is brought close to the object starts to be conspicuous. The above-described condition (5) is a condition which limits a distance between the observation optical system and the illumination optical system. Ideally, the shorter the distance is, the more the illuminance unevenness can be reduced. However, when r/d is 1.3 or less, it is difficult to arrange optical members in such a manner as to prevent them from interfering with one another in the endoscope. When r/d is 3 or more, the illuminance unevenness at the time when the distal end surface of the endoscope is brought close to the object starts to be conspicuous.

Furthermore, in the above-described optical system:

when the distal end surface of the endoscope is formed into a bullet shape assuming the observation optical system as a vertex, at least two of the plurality of illumination optical systems are arranged in such a manner that emission surfaces thereof are directed outwardly with respect to the optical axis of the observation optical system, and an angle between the optical axis of the observation optical system and that of the illumination optical system whose emission surface is outwardly directed is assumed as $\epsilon$, the following condition (6) is more preferably satisfied:

$$5° \leq \epsilon \leq 20° \quad (6).$$

Figure 24:
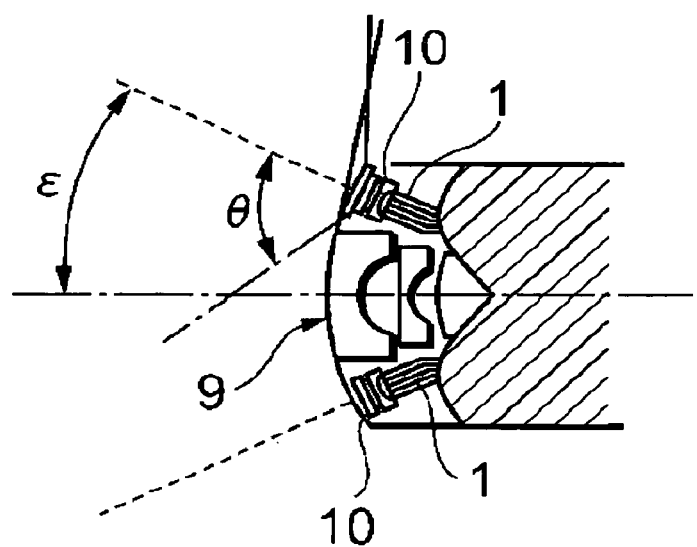
FIG. 24 is a diagram showing one example of a state in which the distal end surface of the endoscope is formed into a bullet shape in which the observation optical system is at a vertex.

In an illumination system which illuminates a visual field of a wide-angle observation optical system having a field angle of 150° or more, as compared with a case where the light is expanded by the illumination optical system alone, a peripheral light quantity is more preferably secured without decreasing illumination efficiency very much in a case where the endoscope distal end surface is formed into a bullet shape assuming the observation optical system or its vicinity as the vertex, and at least two or more illumination optical systems are outwardly tilted as shown in FIG. 24. At this time, the oblique angle $\epsilon$ of the illumination optical system which is outwardly tilted with respect to the observation optical system preferably satisfies $5° \leq \epsilon \leq 20°$.

When the oblique angle $\epsilon$ is smaller than 5°, any significant difference caused by the tilt is not observed. On the other hand, when the oblique angle $\epsilon$ is greater than 20°, the outer diameter of the endoscope distal end portion increases. A light quantity loss or difficulty in assembling, caused by bending of the light guide fiber bundle, raises a problem.

The oblique angle $\epsilon$ more preferably satisfies $5° \leq \epsilon \leq 15°$.

Furthermore, when the endoscope optical system has three illumination optical systems, each of the three illumination optical systems more preferably satisfies the above-described conditions (1) and (2). When each of the three illumination optical systems gives the feeling that it is bright even over a broad area, it is possible to obtain light distribution characteristics having satisfactory symmetry. Especially, when the angle of field increases to about 170°, a need for improvement of the symmetry of the light distribution of the illumination optical system with respect to the whole visual field is heightened. When each illumination optical system satisfies the conditions (1) and (2), light distribution characteristics having satisfactory symmetry are obtained even in such a large angle of field.

The illumination optical system which satisfies the condition (1), or the illumination optical system which satisfies the conditions (1) and (2) more preferably satisfies the following condition (7):

$$0.05 \leq f(80°) \leq 0.15 \quad (7),$$

wherein f(80°) is a value of f($\theta$) at a time when the angle $\theta$ of emission is 80°.

In an illumination system which illuminates a visual field area of an observation optical system having a large field angle, improving the illumination efficiency is one of the important requirements. Light distribution characteristics demanded of the wide-angle illumination optical system are that the illuminance does not change very largely even when the angle of emission is large and that the illuminance gradually decreases from the center of the illumination field to the periphery thereof. The latter is has the purpose of raising the illumination efficiency. For example, the illumination optical system having a high illuminance up to the emission angle of 80° can be said to exhibit a satisfactory performance from the viewpoint of observation. However, to realize the above illumination performance, illumination light having a certain high intensity must be distributed to the area beyond the periphery of the visual field, which need not be illuminated for observation. This is a problem from the viewpoint of illumination efficiency. To avoid the problem, when the relative value of the illuminance of the visual field periphery with respect to that of the visual field center is optimized as shown in the condition (7), illumination having a satisfactory efficiency can be realized. Assuming an illumination system which illuminates the visual field area of an observation optical system having a half field angle of 75° or more, the relative illuminance f(80°) at an emission angle of 80° needs to be 0.05 or more at a minimum. When the illuminance is lower than this value, one feels that the periphery is dark. When the relative illuminance f(80°) exceeds 0.15, the brightness is sufficient, but the outside of the visual field area is excessively illuminated, that is, the illumination efficiency drops.

Figure 26:
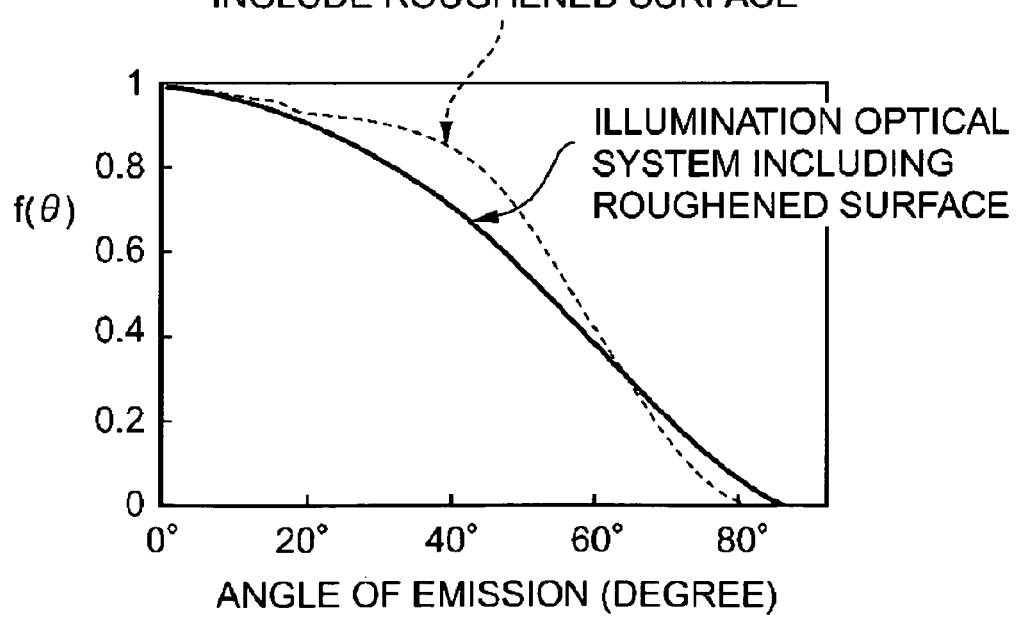
FIG. 26 is a diagram showing spherical light distribution characteristics of the illumination optical system which does not include any roughened surface and those of the illumination optical system including the roughened surface.
Figure 27:
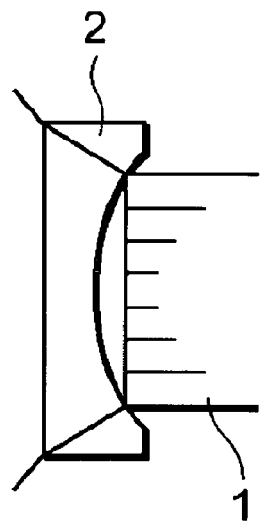
FIG. 27 is a diagram showing a conventional example of an illumination optical system for an endoscope.
Figure 28:
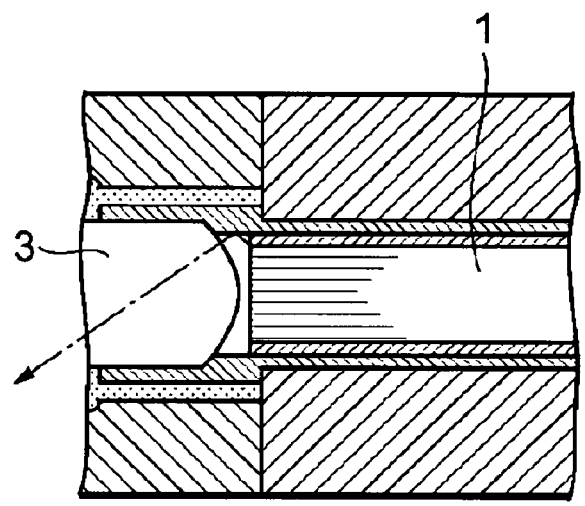
FIG. 28 is a sectional view showing another conventional example of an illumination optical system for an endoscope.
Figure 30:
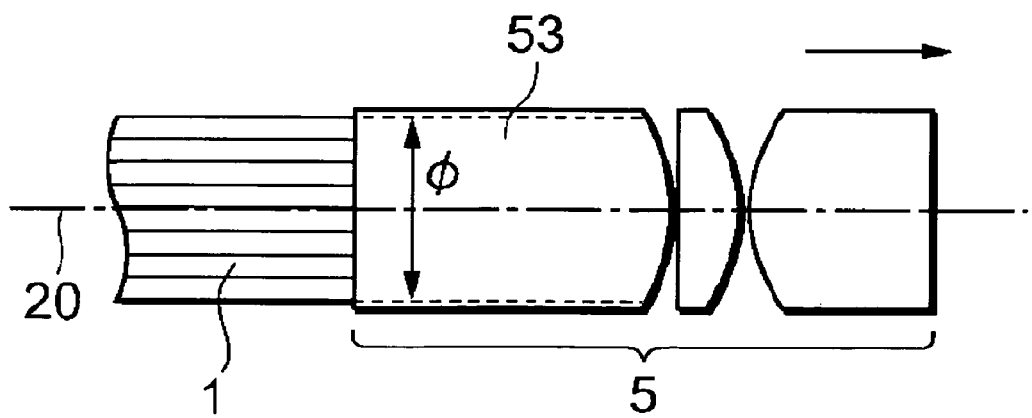
FIG. 30 is a sectional view showing still another conventional example of an illumination optical system an the endoscope.
Figure 29A:
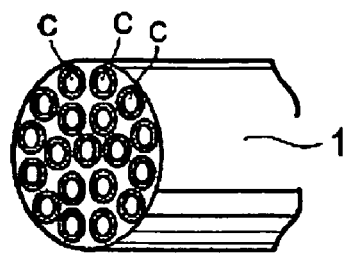
FIG. 29A is a perspective view showing an emission end surface of a light guide fiber bundle.
Figure 29B:
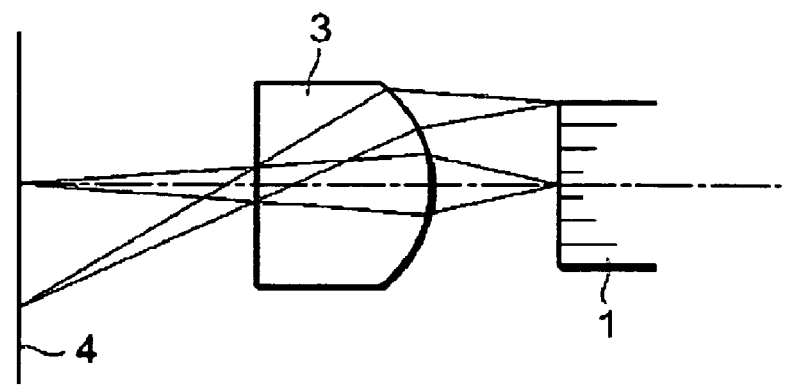
FIG. 29B is a diagram showing a state in which the light emitted from the light guide fiber bundle is projected onto an object surface by the illumination optical system having a positive power.
Figure 29C:
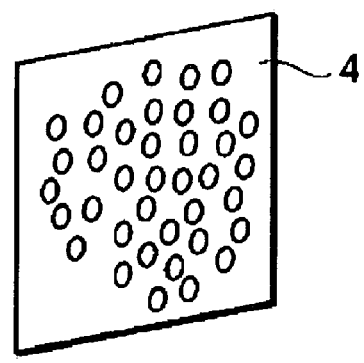
FIG. 29C is a diagram showing a state of the object surface illuminated by the illumination optical system shown in FIG. 29B.
Figure 31:
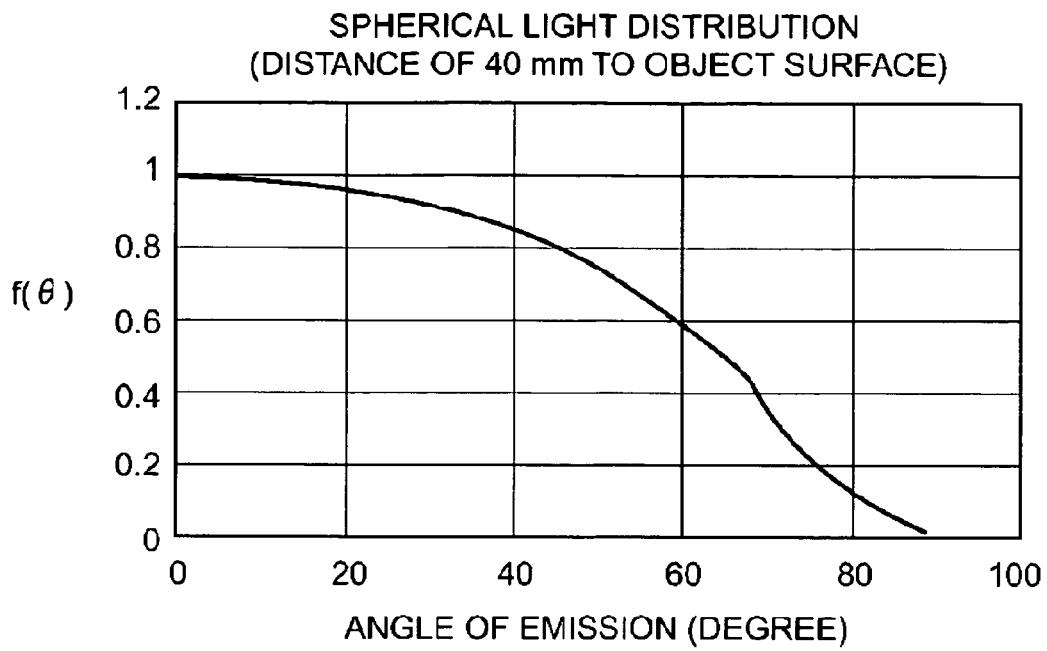
FIG. 31 is a diagram showing one example of the spherical light distribution characteristics of a negative lens shown in FIG. 27.
Figure 32:
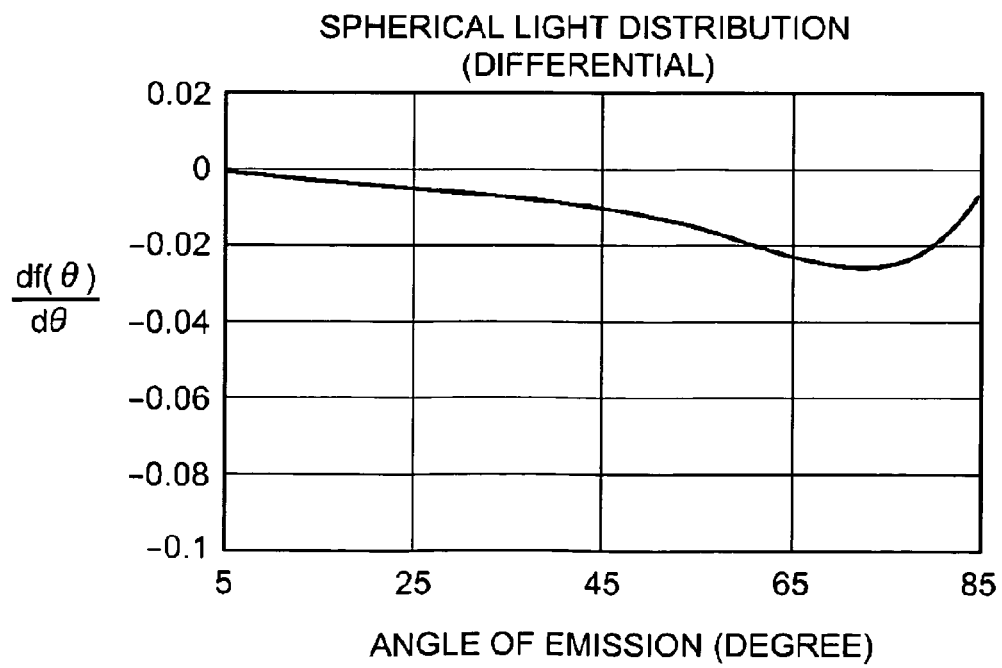
FIG. 32 is a diagram showing differential values of the spherical light distribution characteristics shown in FIG. 31.
Figure 33:
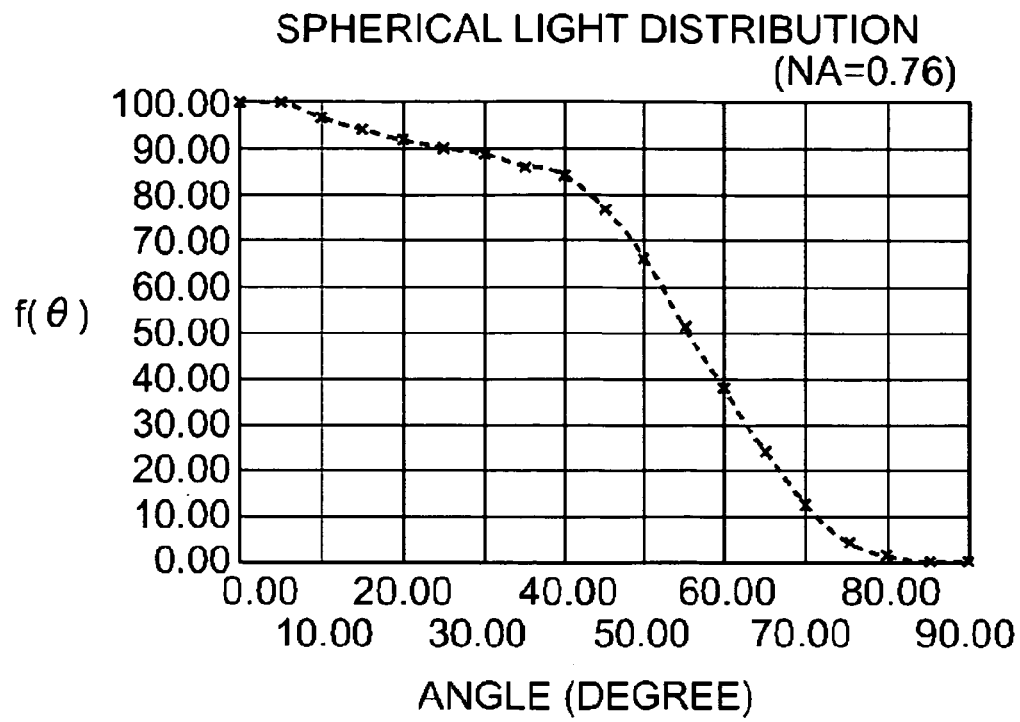
FIG. 33 is a diagram showing spherical light distribution characteristics of the illumination optical system made up of three positive lenses shown in FIG. 30.
Figure 34:
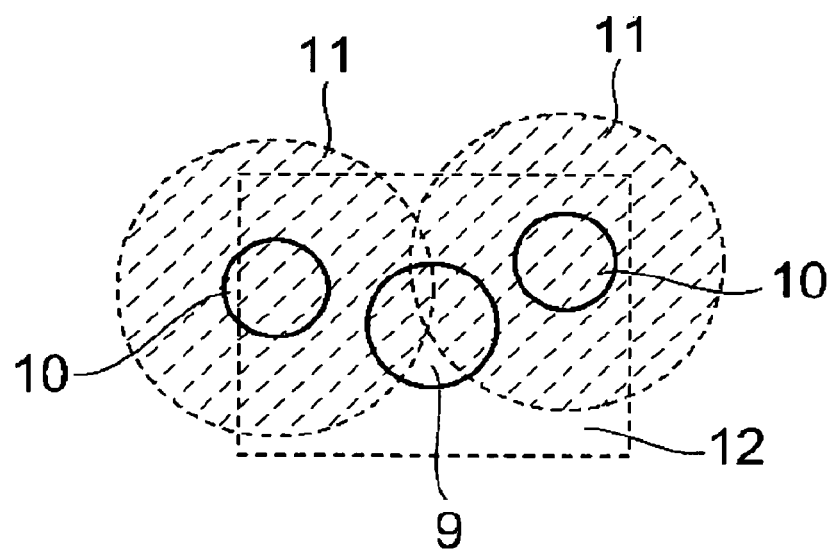
FIG. 34 is a diagram showing a positional relation between an illumination optical system and an observation optical system, and that between an area illuminated by the illumination optical system and a visual field of the observation optical system.
Figure 35:
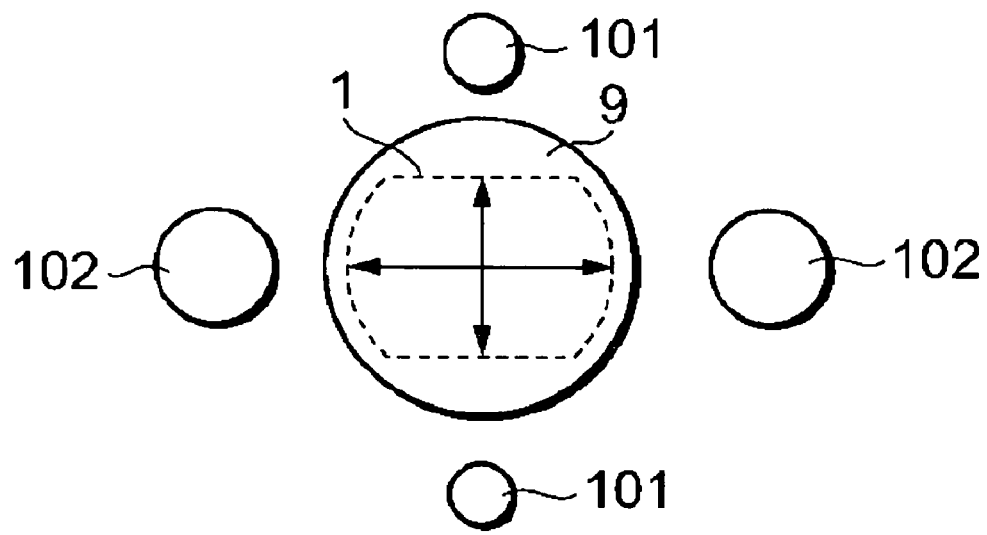
FIG. 35 is a diagram showing an example of a conventional layout of an observation optical system and an illumination optical system in an endoscope.
Figure 36:
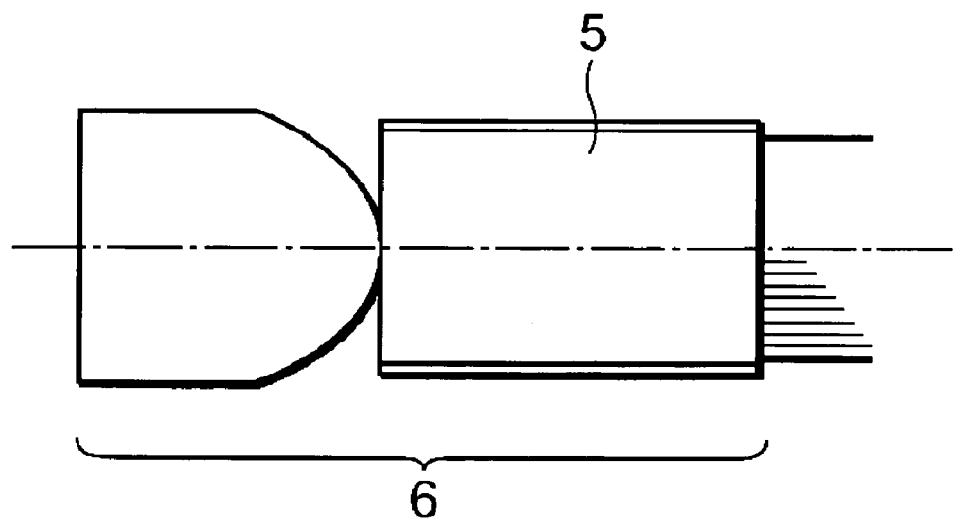
FIG. 36 is a diagram showing one example of a conventional illumination optical system having a single fiber rod between the light guide fiber bundle and a positive lens.

Furthermore, at least one surface of the illumination optical system which satisfies the condition (7) more preferably comprises a roughened surface. In the illumination optical system provided with a roughened surface having a certain roughness level, the light distribution characteristics satisfying the conditions (1) and (2) are easily obtained. FIG. 26 is an explanatory view in which the illuminance obtained by an illumination optical system including a roughened surface is compared with that obtained by an optical system that does not include any roughened surface. As shown by a solid line in the figure, in the illumination optical system provided with the roughened surface, the change of the illuminance in the vicinity of an emission angle of 30° to 50° is moderate as compared with the illumination optical system which does not include any roughened surface. Additionally, a high illuminance is maintained in an area having an angle of emission which is larger than 65° as compared with the illumination optical system which is not provided with any roughened surface. When the illumination optical system has the roughened surface in this manner, the light distribution characteristics desirable for an endoscope having a large angle of field are effectively realized.

Here, definition of the roughened surface in this specification will be described.

The roughened surface is defined by the value of surface roughness of an optical surface. This value is defined by JIS B 0601: 2001 (ISO 4287:1997), and a reference length lr (equal to a cutoff value λc) for obtaining a roughness curve defined herein is calculated as 0.08 mm.

Moreover, "arithmetic average roughness" Ra and "root mean square roughness" Rq defined therein are represented by the following equations:

$$Ra = \frac{1}{lr}\int_0^{lr}|Z(x)|dx$$

$$Rq = \sqrt{\frac{1}{lr}\int_0^{lr}Z^2(x)dx}$$

wherein Z(x) is an ordinate value, and it is a height in a position x of the roughness curve.

In this specification, a surface whose "arithmetic average roughness" Ra defined as above is less than 0.005 is assumed to be a polished surface, and a surface having a value of 0.005 or more is assumed as a roughened surface.

Furthermore, in the illumination optical system, the spherical light distribution characteristics f(θ) in a case where the roughened surface is replaced with the polished surface more preferably satisfy the following condition (8) in at least one of emission angles θ in a range of 0° to 40°, and satisfy the following condition (9) in at least one of emission angles θ in a range of 60° to 70°:

$$-df(\theta)/d\theta \leq 0.015 \qquad (8); \text{ and}$$

$$f(\theta) = 0.02 \qquad (9).$$

The present applicant has found that (virtual) light distribution characteristics at a time when all surfaces crossing the optical axis of the illumination optical system are made of polished surfaces have a large influence on realization of an illumination optical system having the above-described light distribution characteristics for wide-angle illumination. Specifically, it has been found that when at least one surface is worked into the roughened surface in an illumination optical system having flat light distribution characteristics with little change of the spherical surface illuminance up to an emission angle of about 40° and having light distribution characteristics with a large change of the illuminance where the angle of emission is larger, an illumination optical system having the desired light distribution characteristics can be obtained. It has been found that especially in a case where a flat portion having less change of illuminance in the light distribution characteristics curve is larger, when at least one surface in the illumination optical system is formed into a roughened surface, performances suitable for wide-angle illumination are obtained. The present applicant also has found that, in an illumination system whose illuminance largely drops off before the angle of emission reaches 40°, it is difficult to illuminate the wide-angle portion even when a roughened surface is introduced into the illumination system.

The illumination optical system which satisfies the condition (7) more preferably comprises one plano-convex lens having a positive power, and the convex surface thereof is an aspherical surface worked as the roughened surface. When the curved surface of the lens is an aspherical surface, the light distribution performances can be freely changed as compared with a spherical surface. Therefore, when the roughened surface is formed on the aspherical surface, the light can be more widely distributed owing to a diffusing effect of the surface. It is to be noted that assuming that an optical axis direction is Z, a height from the optical axis is y, and a light traveling direction is positive, the shape of the aspherical surface is represented by the following equation:

$$Z(y) = \frac{(1/R) \cdot y^2}{1 + \sqrt{\{1 - (k+1) \cdot (1/R)^2 \cdot y^2\}}} + A2 \cdot y^2 + A4 \cdot y^4 + \ldots + An \cdot y^n$$

wherein R is a radius of curvature of a lens surface, k is a conical coefficient, A2 is a second order aspherical coefficient, A4 is a fourth order aspherical coefficient, and An is an n-th order aspherical coefficient. Since the shape of the lens surface is symmetric with the optical axis, the shape needs to be made up of even terms in this manner.

Here, when the convex surface is formed into an aspherical surface, by using only one lens, the illuminance in an emission angle range of 30° to 50° can be raised to an illuminance substantially equal to that in the spherical light distribution characteristics which can be achieved by three positive lenses. The present applicant has found that when this aspherical surface is formed into a roughened surface having an appropriate roughness level, it is possible to obtain spherical light distribution characteristics having little change of illuminance. When the roughened surface is formed on an aspherical surface, a dot-matrix-like illuminance unevenness can be eliminated by the diffusing effect. Therefore, the illumination optical system can be formed of one lens, and costs can be reduced. In a case where the illumination optical system is obliquely disposed with respect to the optical axis of the observation optical system, the total length of the illumination optical system needs to be shortened in order to reduce the diameter of the distal end portion of the endoscope. However, the illumination optical system composed of only one lens can also satisfy a demand that the total length of the illumination optical system be shortened.

Embodiments of the present invention will be described hereinafter with reference to the drawings.

Figure 1:
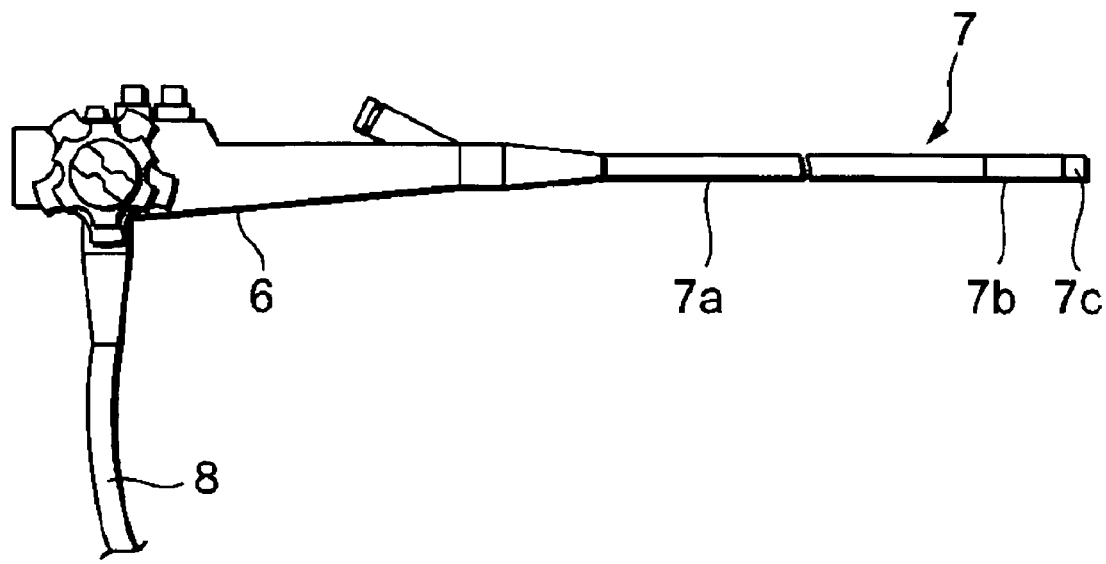
FIG. 1 is a diagram showing one example of an endoscope to which an endoscope optical system of the present invention is applicable.

FIG. 1 is a diagram showing one example of an endoscope to which the endoscope optical system of the present invention is applicable. In FIG. 1, reference numeral 6 denotes an operation section which is to be manually grasped and operated by an operator or the like, 7 denotes an insertion section to be inserted into a body cavity or the like, and 8 denotes a universal cord. The insertion section 7 comprises a flexible portion 7a which is disposed continuously from the operation section 6 and whose major part in the length direction can be bent along an insertion path; an angling portion 7b connected to the tip of this flexible portion 7a; and a hard distal end portion 7c connected to the angling portion 7b. The angling portion 7b directs the hard distal end portion 7c in a desired direction. The hard distal end portion 7c is provided with a mechanism for observing the inside of the body cavity. Moreover, the endoscope optical system of the present invention is disposed in the hard distal end portion 7c.

Figure 2:
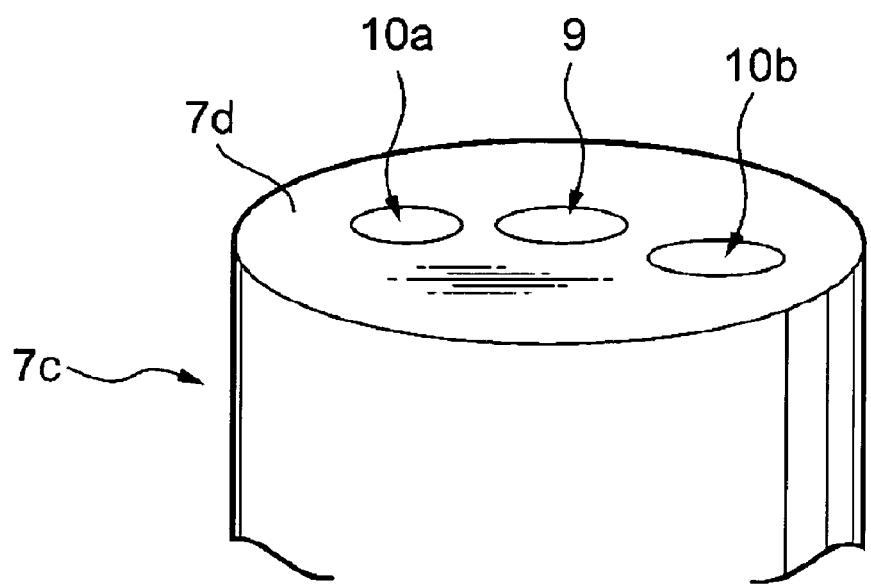
FIG. 2 is an enlarged perspective view of a distal end portion of the endoscope according to Embodiment 1 of the present invention.

FIG. 2 is an explanatory view showing the optical system of the distal end portion of the endoscope according to Embodiment 1 of the present invention. In FIG. 2, a distal end surface 7d of the hard distal end portion 7c of the endoscope is formed substantially into a flat shape. On the surface, there are arranged: an observation optical system 9 having a field angle of 155°; and two illumination optical systems 10a and 10b. It is to be noted that although not shown for the sake of simplification, the distal end surface 7d of the endoscope is provided with an opening via which treatment tools such as forceps are inserted/removed, and a nozzle for supplying a fluid for cleaning toward the distal end surface of the observation optical system. End surfaces of the illumination optical systems 10a and 10b on their image side are brought into contact with an end surface of a light guide fiber bundle (not shown).

It is to be noted that light distribution characteristics of illumination light exiting from the emission end surface of the light guide fiber bundle are largely influenced by those of light from a light source, which enters an incidence end surface of the light guide fiber bundle. However, a numerical aperture (NA) of the light guide fiber bundle is determined by refractive indices of media constituting the core and cladding of an optical fiber. That is, assuming that the refractive indices of the materials of the core and cladding of the optical fiber in the light guide fiber bundle are $n_1$, $n_2$, respectively, the numerical aperture can be represented by:

$$NA=(n_1^2-n_2^2)^{1/2}=\sin \alpha,$$

wherein $\alpha$ is the incidence angle of the illumination light upon the light guide fiber bundle.

Figure 3:
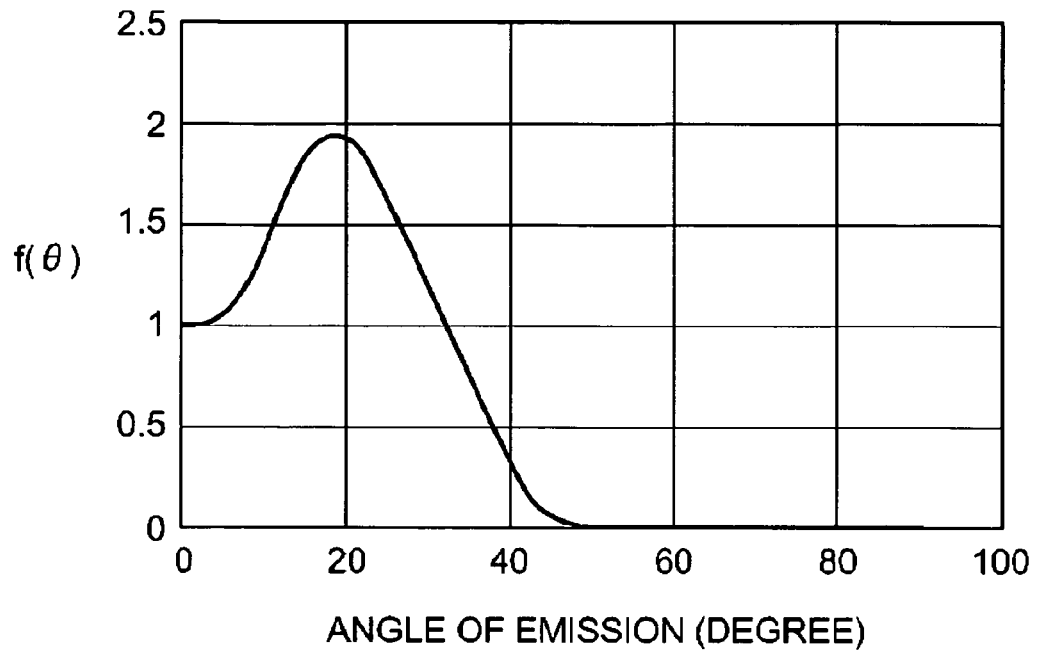
FIG. 3 is a diagram showing light distribution characteristics in an emission end of a light guide fiber bundle for use in Embodiment 1.

It is common that a high-NA optical fiber is used in the light guide fiber bundle of the endoscope in order to raise the light transmission efficiency. More specifically, as to each of the optical fibers for use in the light guide fiber bundle, the refractive indices of the media constituting the core and cladding are 1.65, 1.51, respectively, and NA=0.66 ($\alpha$=46°). The light distribution characteristics in the emission end of the light guide fiber bundle are shown in FIG. 3.

Figure 4:
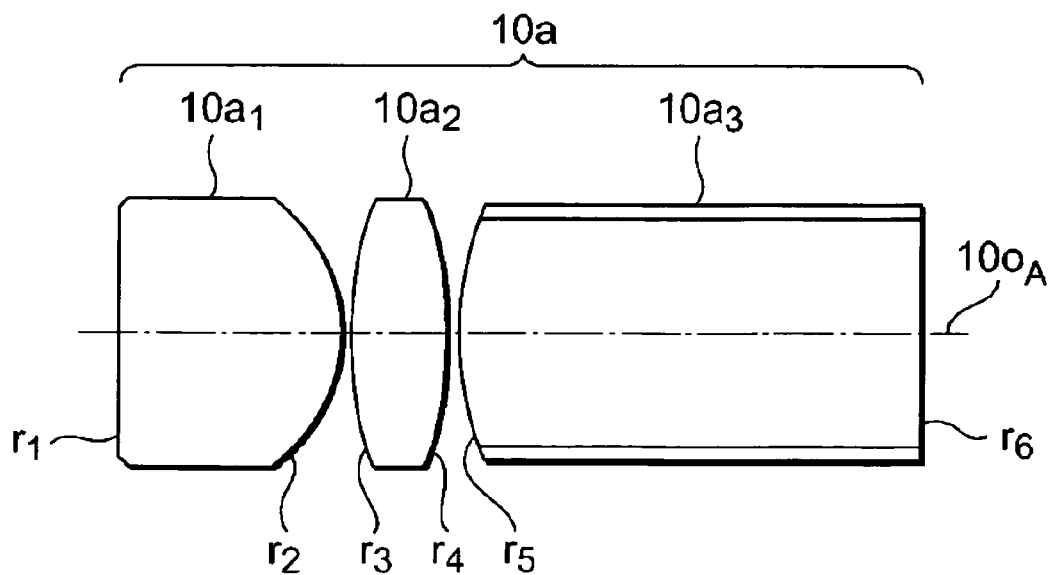
FIG. 4 is a sectional view along an optical axis of the illumination optical system 10a shown in FIG. 2.

Next, the two illumination optical systems 10a and 10b of Embodiment 1 will be described. FIG. 4 is a sectional view along the optical axis of the illumination optical system 10a of the endoscope optical system shown in FIG. 2. The illumination optical system 10a comprises a plano-convex lens $10a_1$ having a flat surface on its object side and a convex surface on its image side; a double-convex lens $10a_2$; and a plano-convex lens $10a_3$ having a convex surface on its object side and a flat surface on its image side, and the lenses are arranged in order from the object side. The plano-convex lens $10a_3$ is composed of a single fiber rod. Reference numeral $10_{oA}$ denotes the optical axis.

Figure 5:
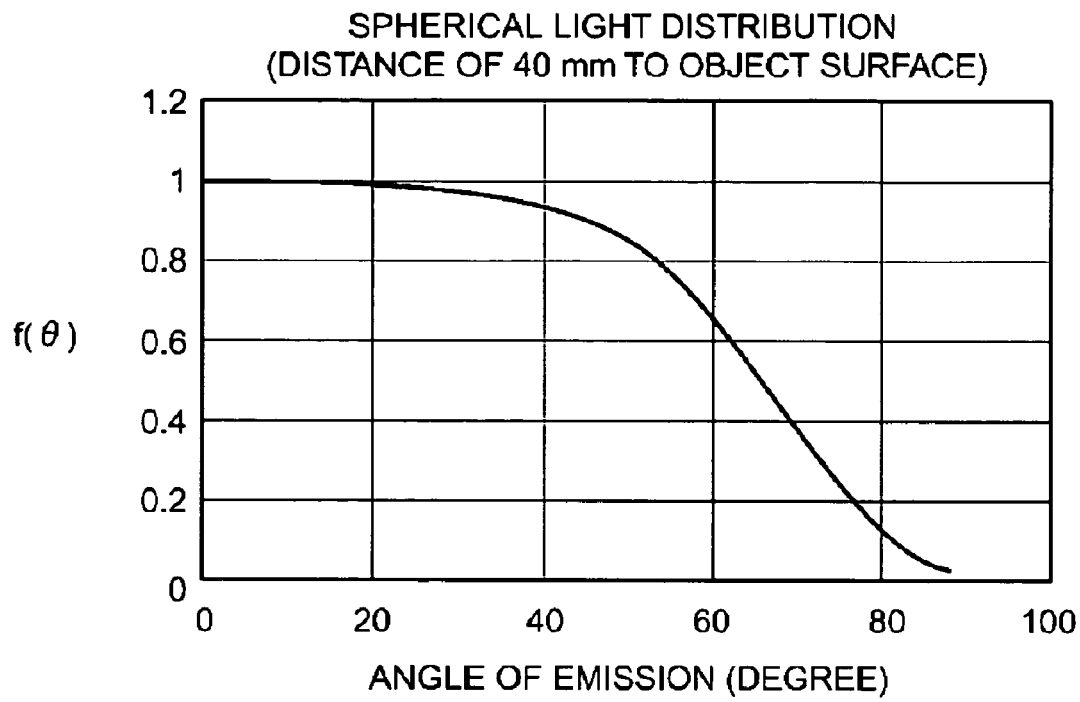
FIG. 5 is a diagram showing spherical light distribution characteristics f(θ) of the illumination optical system 10a of Embodiment 1.
Figure 6:
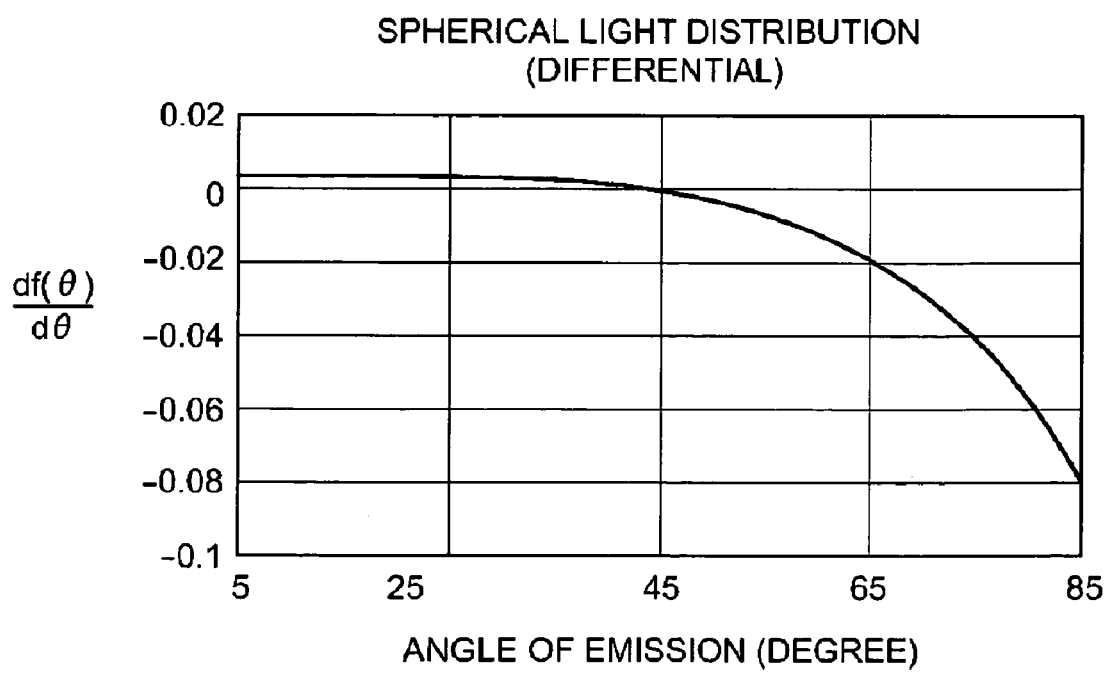
FIG. 6 is a diagram showing differential values df(θ)/dθ of the light distribution characteristics f(θ) of the illumination optical system 10a of Embodiment 1.

FIG. 5 shows light distribution characteristics $f(\theta)$ of the illumination optical system 10a, and FIG. 6 shows differential values $df(\theta)/d\theta$ of the light distribution characteristics $f(\theta)$.

Figure 7:
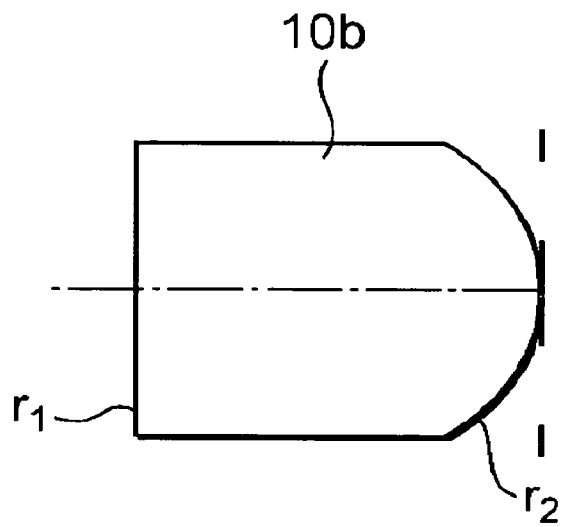
FIG. 7 is a sectional view along an optical axis of the illumination optical system 10b shown in FIG. 2.

FIG. 7 is a sectional view along an optical axis of the illumination optical system 10b in the endoscope optical system shown in FIG. 2. The illumination optical system 10b comprises one positive lens having a flat surface on its object side and a convex aspherical surface on its image side, and the portion (convex aspherical surface) having a curvature is roughened.

Figure 8:
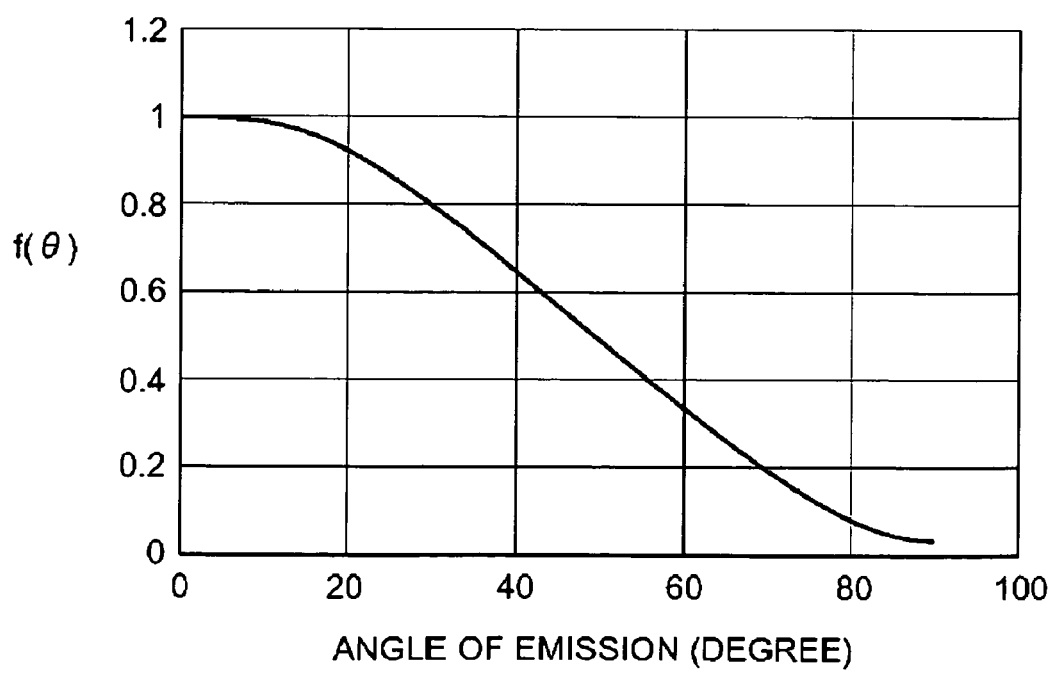
FIG. 8 is a diagram showing the light distribution characteristics f(θ) of the illumination optical system 10b of Embodiment 1.
Figure 9:
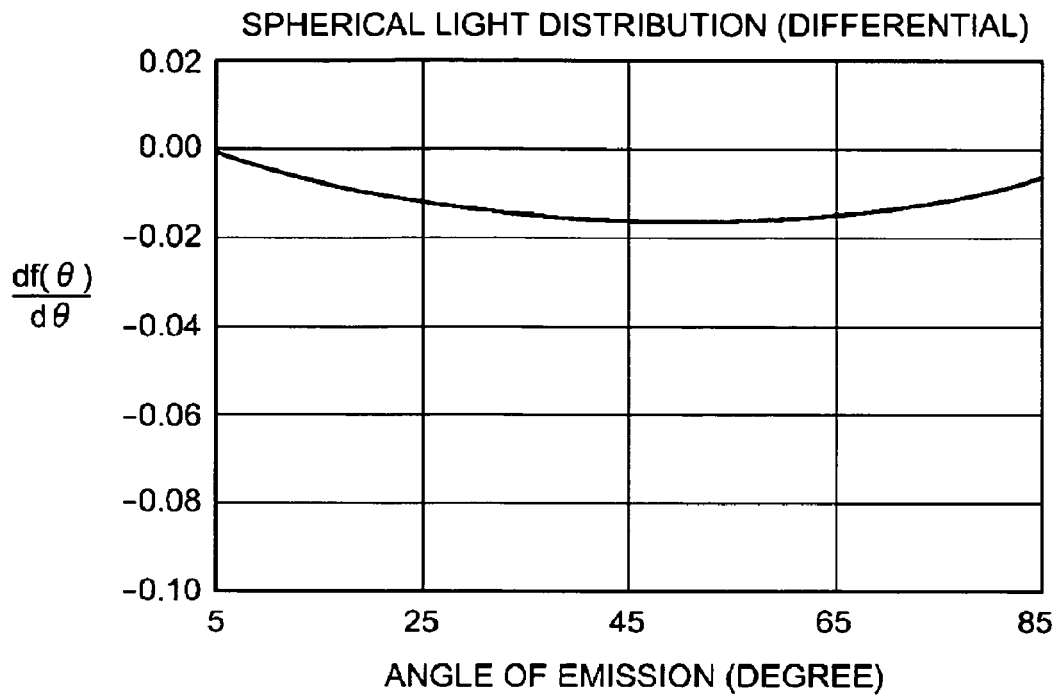
FIG. 9 is a diagram showing the differential values df(θ)/dθ of the light distribution characteristics f(θ) of the illumination optical system 10a of Embodiment 1.

FIG. 8 shows the light distribution characteristics $f(\theta)$ of the illumination optical system of FIG. 10b, and FIG. 9 shows differential values $d(f\theta)/d\theta$ of the light distribution characteristics $f(\theta)$.

Additionally, in graphs of FIGS. 5 and 8 showing the light distribution characteristics $f(\theta)$, the abscissa shows the angle $\theta$ of emission from an illumination lens, the ordinate indicates the relative illuminance $f(\theta)$ on a spherical object, and the quantity of light at $\theta$=0° is 1. In the graph of a differential function $df(\theta)/d\theta$, the abscissa indicates the angle $\theta$ of emission from the illumination lens, and the ordinate indicates the differential values of the light distribution characteristics.

Figure 10:
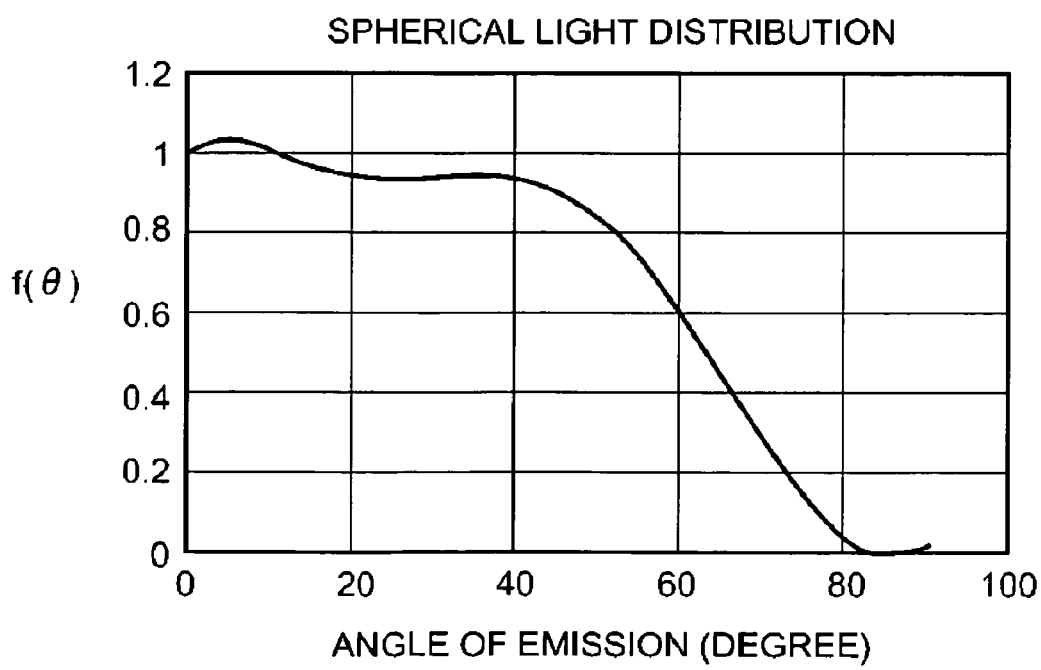
FIG. 10 is a diagram showing the light distribution characteristics f(θ) in a case where a roughened surface in the illumination lens 10b of Embodiment 1 is replaced with a polished surface.
Figure 11:
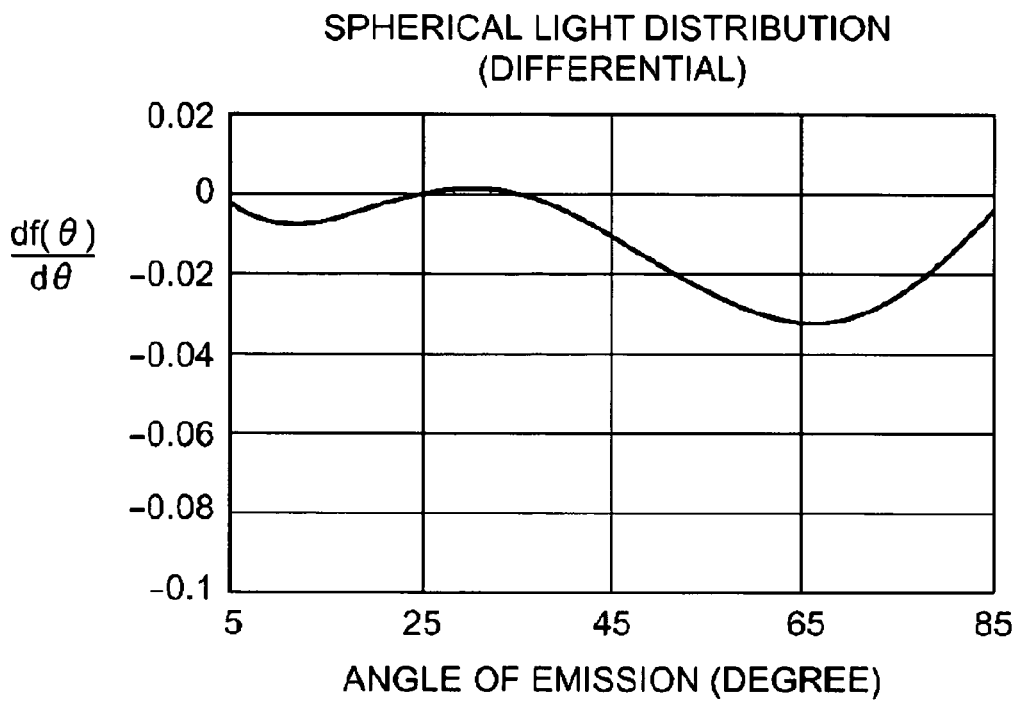
FIG. 11 is a diagram showing the differential values df(θ)/dθ of the light distribution characteristics f(θ) in the case where the roughened surface in the illumination lens 10b of Embodiment 1 is replaced with the polished surface.

Here, the light distribution characteristics of the illumination optical system 10b will be described in detail. If the roughened surface in the illumination lens 10b of Embodiment 1 is replaced with a polished surface, the light distribution characteristics shown in FIG. 10 are obtained. A graph of the differential values $df(\theta)/d\theta$ of the light distribution characteristics $f(\theta)$ at this time is shown in FIG. 11. As shown in FIG. 11, this illumination optical system exhibits light distribution performances such that $-df(\theta)/d\theta$ is 0.01 or less at an angle $\theta$ of emission in a range of 5° to 40°, and $-df(\theta)/d\theta$ is 0.03 in the vicinity of where the angle $\theta$ of emission is 65°.

When the curved surface of the illumination optical system having such light distribution performances is worked into a roughened surface having a certain roughness level, it is possible to obtain an illumination optical system suitable for a wide-angle illumination system.

The present applicant has found out that when the surface is roughened in such a manner as to obtain a roughened surface having an "arithmetic average roughness" Ra=0.1 to 0.6 μm, $-df(\theta)/d\theta$ of the illumination optical system 10b of Embodiment 1 retains a value of 0.02 or less at an angle $\theta$ of emission in the range of 5° to 85°, and further retains a value of 0.015 or less at an angle $\theta$ of emission in the range of 65° to 80°, and therefore it is possible to give the impression that no change of brightness is felt from the visual field center to the periphery. It has also become clear that the illuminance ratio f(θ) at an angle θ of emission =80° is 0.09, and the system also has a superior performance in terms of its illumination efficiency.

Here, in addition to the roughened surface formed on the curved surface, examples of a construction capable of realizing the above-described light distribution characteristics include: a lens formed by cementing a large number of micro ball lenses or an inner diffusion element; a curved surface whose sectional shape is represented by a differentiable periodic function; a shape obtained by approximating the differentiable curved surface with a plurality of straight lines; and the like. However, considering the aspects of ease of working the lens, and the lens evaluation method, the roughened surface is preferable.

The illumination optical system 10a is similar to a conventional illumination optical system mainly used for illuminating the visual field of an observation optical system having a field angle of 140°. As shown in FIG. 5, the change of the illuminance increases in a range of angles of emission exceeding 60°. Therefore, in an endoscope having a field angle of 150° (half field angle of 75°) or more, the visual field periphery darkens.

Figure 12:
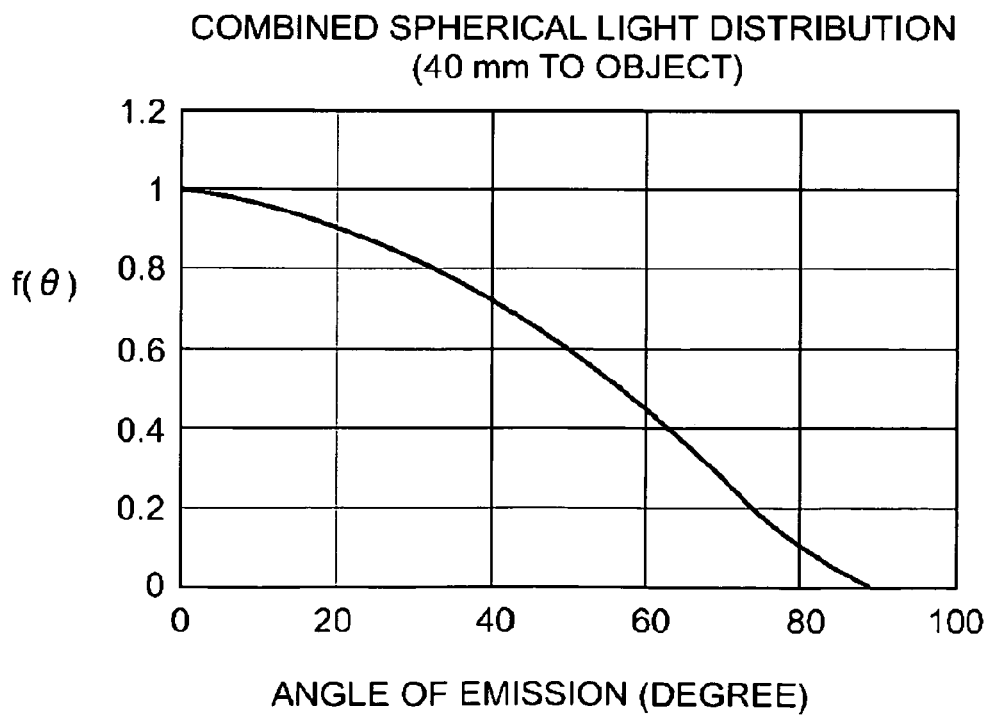
FIG. 12 is a diagram showing spherical light distribution characteristics at a time when an object to be illuminated is disposed in a position at a distance of 40 mm from a center of the lens closest to an object side of the observation optical system, and the object is illuminated using the illumination optical system formed by combining two illumination optical systems 10a and 10b.

On the other hand, as to the light distribution characteristics of an illumination optical system in which two illumination optical systems 10a and 10b are combined, as shown in FIG. 12, the illuminance is moderately dampened until the angle of emission reaches 0° to 80°. Therefore, it is possible to obtain an illumination system which is sufficiently usable even in an endoscope having a field angle of 150° or more. Additionally, FIG. 12 is a graph showing the spherical light distribution characteristics at a time when an object to be illuminated is disposed in a position at a distance of 40 mm from the center of the lens closest to the object side of the observation optical system, and the object is illuminated using the illumination optical system obtained by combining two illumination optical systems 10a and 10b.

Next, numerical data of the illumination optical system of Embodiment 1 will be described. In the numerical data: $r_1$, $r_2$ ... denote radii of curvature of lens surfaces and the like; $d_1$, $d_2$ ... denote thicknesses or air intervals of lenses and the like; $n_{d1}$, $n_{d3}$ ... denote refractive indices of materials of the respective lenses and the like at the wavelength of the d-line; and $v_{d1}$, $v_{d3}$ ... denote Abbe numbers of the materials of the respective lenses and the like at the wavelength of the d-line. These symbols are common to the respective embodiments.

Numerical Data 1

| Illumination optical System 10a | | | |
|---|---|---|---|
| $r_1 = \infty$ | $d_1 = 1.5$ | $n_{d1} = 1.883$ | $v_{d1} = 40.76$ |
| $r_2 = -1.116$ | $d_2 = 0.07$ | | |
| $r_3 = 2.858$ | $d_3 = 0.655$ | $n_{d3} = 1.883$ | $v_{d3} = 40.76$ |
| $r_4 = -2.858$ | $d_4 = 0.07$ | | |
| $r_5 = 2.11$(single fiber rod) | $d_5 = 3.2$ | $n_{d5} = 1.72825$ | $v_{d5} = 28.46$ |
| $r_6 = \infty$ | $d_6 = 0$ | | |
| $r_7 = \infty$(emission end surface of light guide fiber bundle) | | | |

Focal length: 0.702 mm

| Illumination optical System 10b | | | |
|---|---|---|---|
| $r_1 = \infty$ | $d_1 = 1.85$ | $n_{d1} = 1.883$ | $v_{d1} = 40.76$ |
| $r_2 = -0.675$(aspherical surface) | | | |
| $r_3 = \infty$(emission end surface of light guide fiber bundle) | | | |

Figure 13:
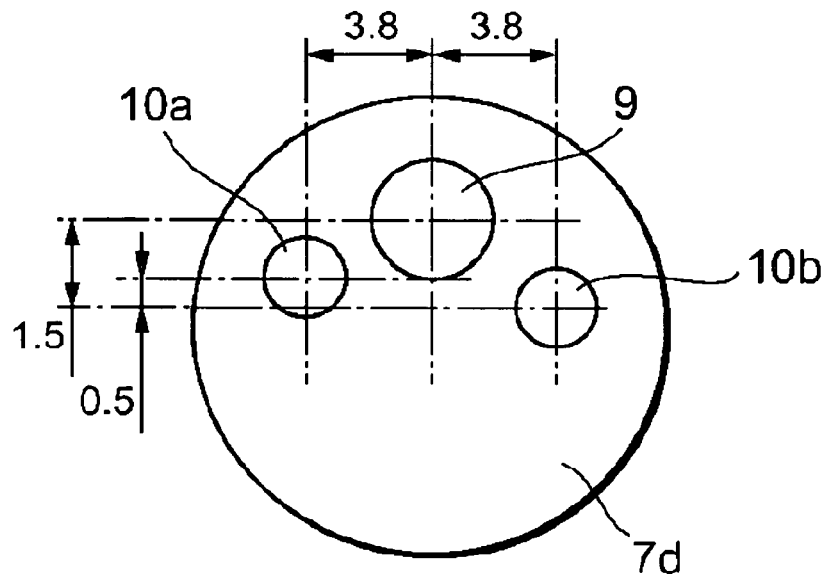
FIG. 13 is a front view of the distal end surface of the endoscope in Embodiment 1.

Aspherical surface data (second surface)
k = −0.625, A4 = −0.1
Focal length: 0.7644 mm FIG. 13 shows dimensional data of the observation optical system and the illumination optical system in Embodiment 1. This figure is a view of the distal end surface 7d of the endoscope shown in FIG. 2 as seen from the front. The units of the numerical values are in mm.

Embodiment 2

Figure 14:
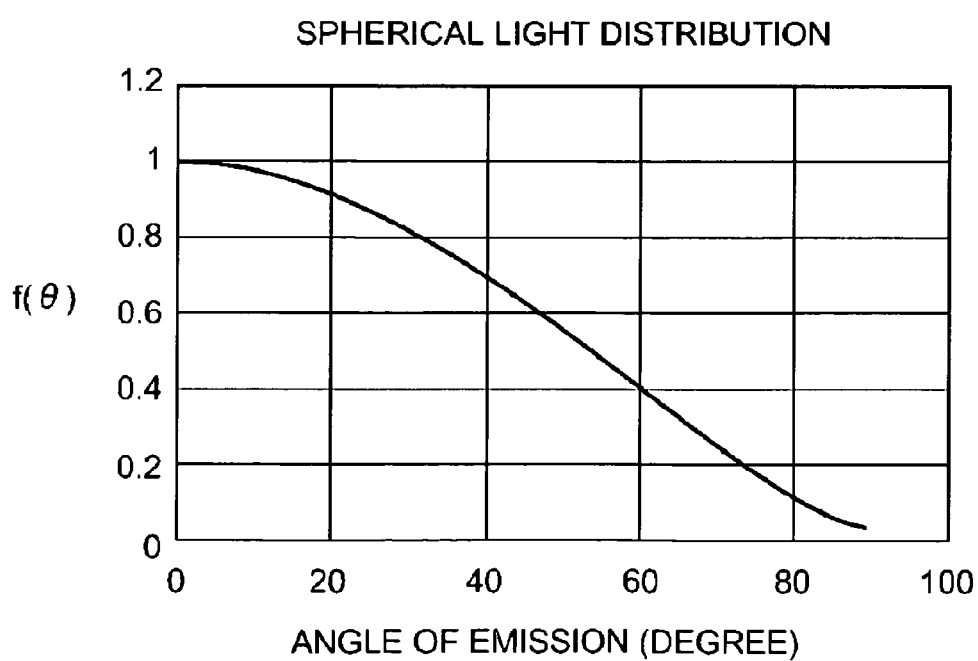
FIG. 14 is a diagram showing the light distribution characteristics f(θ) of the illumination optical system 10b in the endoscope optical system of Embodiment 2.
Figure 15:
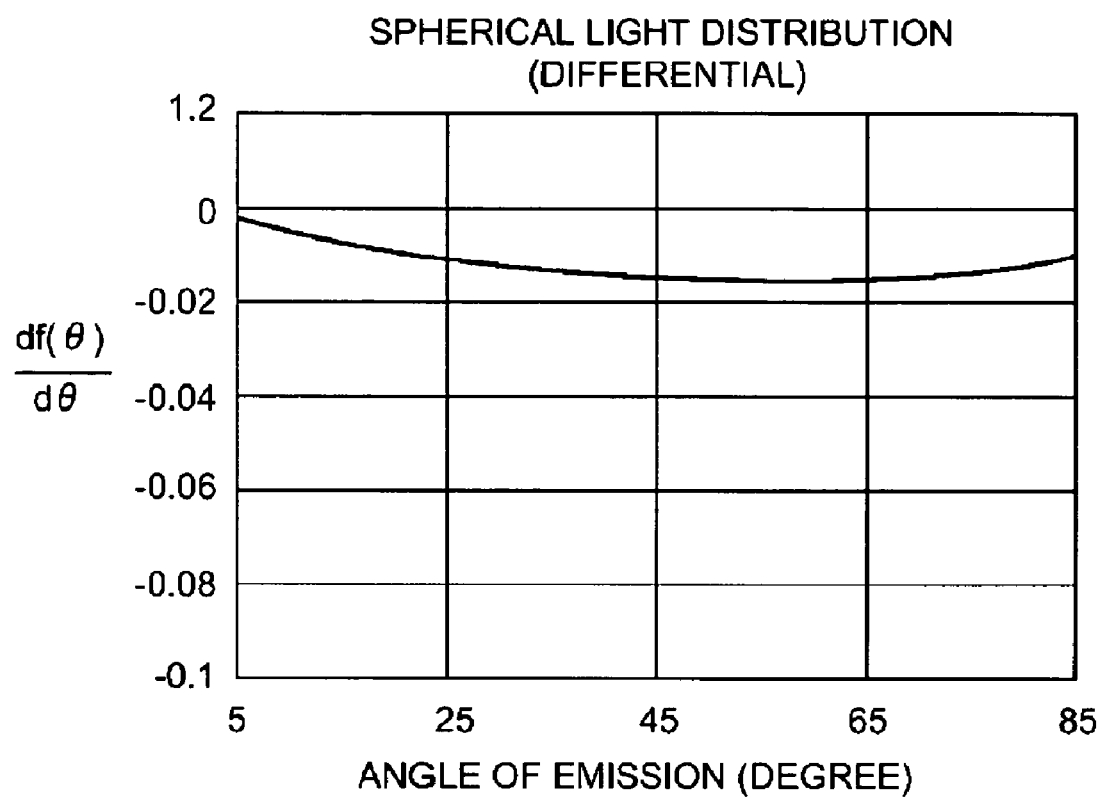
FIG. 15 is a diagram showing the differential values df(θ)/dθ of the light distribution characteristics f(θ) of the illumination optical system 10b of Embodiment 2.

The basic arrangement of the endoscope optical system of Embodiment 2 is substantially the same as that of Embodiment 1, and is different from that of Embodiment 1 in that the convex surface of the illumination optical system 10b is finished as a polished surface. The illumination optical system 10b has light distribution characteristics f(θ) shown in FIG. 14. Differential values df(θ)/dθ of the light distribution characteristics f(θ) are shown in FIG. 15. As shown in FIG. 15, the differential value df(θ)/dθ of the light distribution characteristics f(θ) retains a value of 0.02 or less at an angle θ of emission in the range of 5° to 85°, and further retains a value of 0.015 or less at the angle θ of emission in the range of 65° to 80°. Therefore it is possible to give the impression that no change of brightness is felt from the visual field center to the periphery. Furthermore, the illuminance ratio f(θ) at an emission angle θ of 80° is 0.11, and the system also has a superior performance in terms of its illumination efficiency.

Next, numerical data of the illumination optical system 10b forming the optical system of a distal end portion of the endoscope of Embodiment 2 will be described. It is to be noted that since the illumination optical system 10a of Embodiment 2 is the same as that of Embodiment 1, description of numerical data thereof is omitted.

Numerical Data 2

| Illumination optical System 10b | | | |
|---|---|---|---|
| $r_1 = \infty$ | $d_1 = 1.85$ | $n_{d1} = 1.883$ | $v_{d1} = 40.76$ |
| $r_2 = -0.781$(polished surface) | | | |
| $r_3 = \infty$(emission end surface of light guide fiber bundle) | | | |

Focal length: 0.8794 mm

Embodiment 3

Figure 16A:
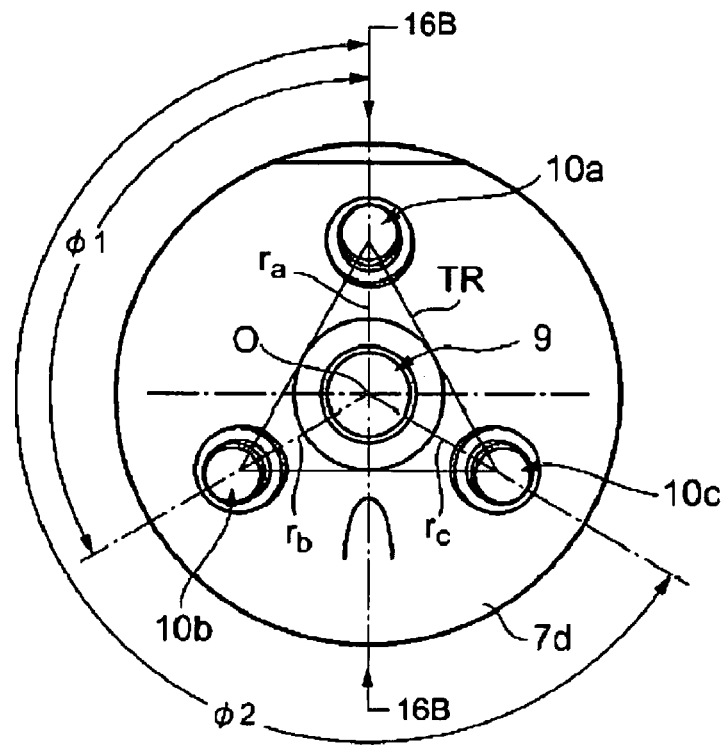
FIGS. 16A and 16B are diagrams showing Embodiment 3 of the present invention.
Figure 16B:
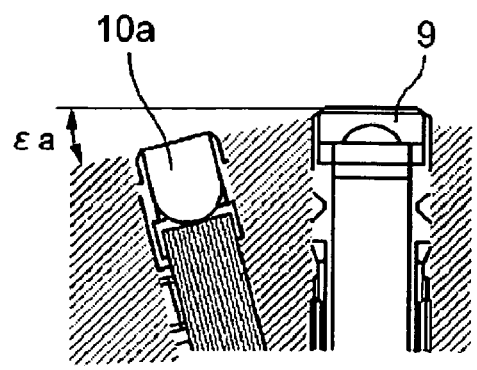

FIGS. 16A and 16B are diagrams showing Embodiment 3 of the present invention, FIG. 16A is a diagram of a layout of an endoscope optical system as viewed from the object side, and FIG. 16B is a diagram showing a part of a section along line 16B-16B of FIG. 16A.

The endoscope optical system of Embodiment 3 is provided with an observation optical system 9 having a field angle of 170°, and three illumination optical systems 10a, 10b and 10c. The distal end surface 7d of the endoscope is formed into a bullet shape in which the observation optical system is at the vertex. As viewed from the front (object side), the three illumination optical systems 10a, 10b and 10c are arranged in such a manner as to surround the observation optical system 9. The three illumination optical systems 10a, 10b and 10c are oblique in such a manner as to direct emission surfaces thereof outwardly with respect to the optical axis of the observation optical system in accordance with the bullet shape of the distal end surface 7d. The oblique angles εa, εb and εc of each the three illumination optical systems 10a, 10b and 10c is 7°.

Each of the three illumination optical systems 10a, 10b and 10c comprises one positive lens as shown in FIG. 7.

Moreover, as shown in FIG. 16, the three illumination optical systems 10a, 10b and 10c are arranged in such a manner that a center O of a lens closest to the object side of the observation optical system 9 is positioned in the area of a triangle TR made by mutually connecting centers of lenses closest to the object sides of the three illumination optical systems 10a, 10b and 10c.

Furthermore, assuming that the direction of a straight line connecting the center of the lens closest to the object side of the observation optical system 9 to that of the lens closest to the object side of the illumination optical system 10a is 0°, angles φ1, φ2 in directions of straight lines connecting the center of the lens closest to the object side of the observation optical system 9 to the centers of the lenses closest to the object sides of the illumination optical systems 10b and 10c are 120° and 240°, respectively. Distances ra, rb and rc from the center of the lens closest to the object side of the observation optical system 9 to the centers of the lenses closest to the object sides of the illumination optical systems 10a, 10b and 10c are 4.5 mm, 4.7 mm, and 5 mm, respectively. The outer diameter of the lens closest to the object side of the observation optical system 9 is 2.3 mm.

In Embodiment 3, since the three illumination optical systems 10a, 10b and 10c are arranged with respect to the observation optical system 9 as described above, it is possible to secure a well-balanced light distribution performance even in a case where the distal end surface of the endoscope comes close to an object surface.

Figure 17:
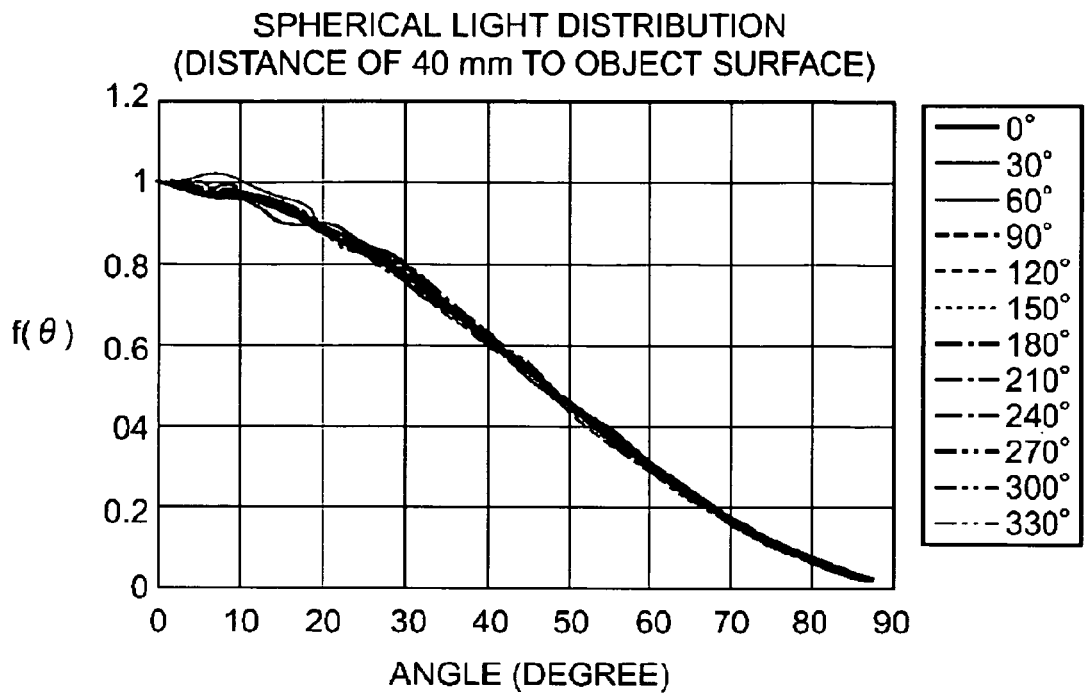
FIG. 17 is a diagram showing light distribution characteristics for each direction in a visual field at a time when the spherical object disposed at a distance of 40 mm from the distal end surface of the endoscope is illuminated by three illumination optical systems 10a, 10b and 10c in Embodiment 3.
Figure 18:
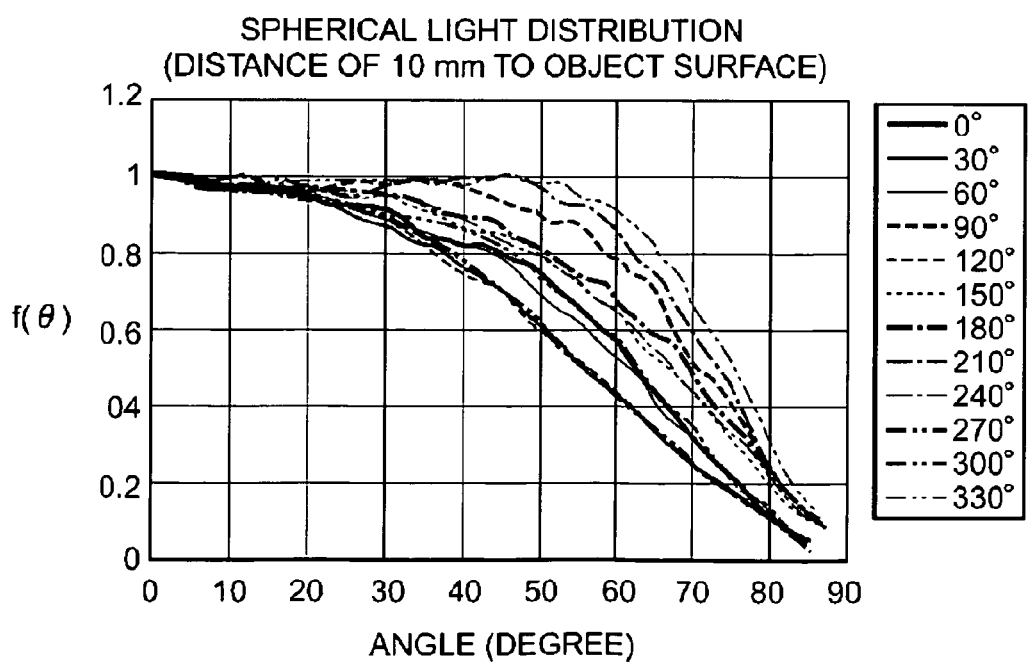
FIG. 18 is a diagram showing light distribution characteristics for each direction in the visual field at a time when the spherical object disposed at a distance of 10 mm from the distal end surface of the endoscope is illuminated by three illumination optical systems 10a, 10b and 10c in Embodiment 3.

FIG. 17 is a graph showing light distribution characteristics on the object surface at a time when a spherical object disposed at a distance of 40 mm from the distal end surface of the endoscope is illuminated simultaneously by the three illumination optical systems 10a, 10b and 10c. Numerical values such as 0° and 30° shown on the right outside the frame of the figure designate azimuthal angles of straight lines extending in radial directions from the center of the visual field in the visual field of the observation optical system. The graph shown by types of lines in the figure indicates the relation between the field angle and the illuminance ratio in the corresponding direction. An azimuthal angle of 0° indicates the direction of a straight line which connects the center O of the lens closest to the object side of the observation optical system to the center of the lens closest to the object side of the illumination optical system 10a. The origin (reference point of the angle of field) is the center of the distal end surface of the observation optical system 9. FIG. 18 is a similar graph for the case where the distance from the distal end surface of the endoscope to the surface of the spherical object is 10 mm.

As shown in FIG. 17, when the distance to the object (object surface) is 40 mm, there is little fluctuation of the light distribution characteristics depending on the direction in the visual field. When this fluctuation is large, such an illuminance unevenness is generated that a certain direction is dark, but another direction is bright. Even in the case where the object is positioned in a short distance, for example, 10 mm from the distal end surface of the endoscope, as shown in FIG. 18, the light distribution characteristics are well balanced, and the illuminance unevenness is inconspicuous.

Figure 19:
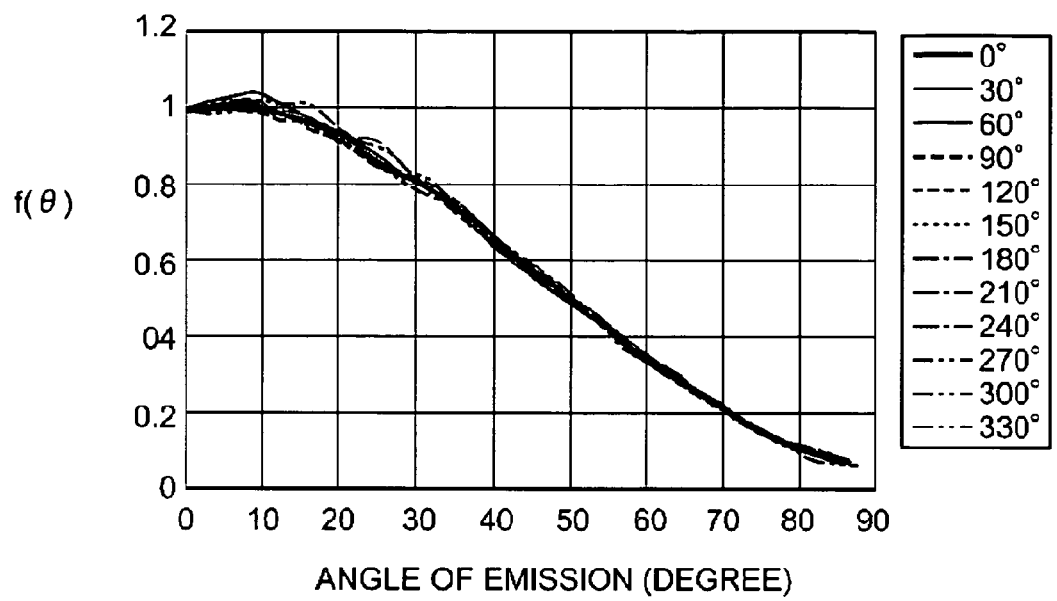
FIG. 19 is a diagram showing spherical light distribution characteristics on an object surface disposed at a distance of 40 mm from the distal end surface of the endoscope at a time when each of oblique angles εa, εb, εc of three illumination optical systems is set to 15° in the endoscope optical system having the light distribution characteristics shown in FIG. 17.
Figure 20:
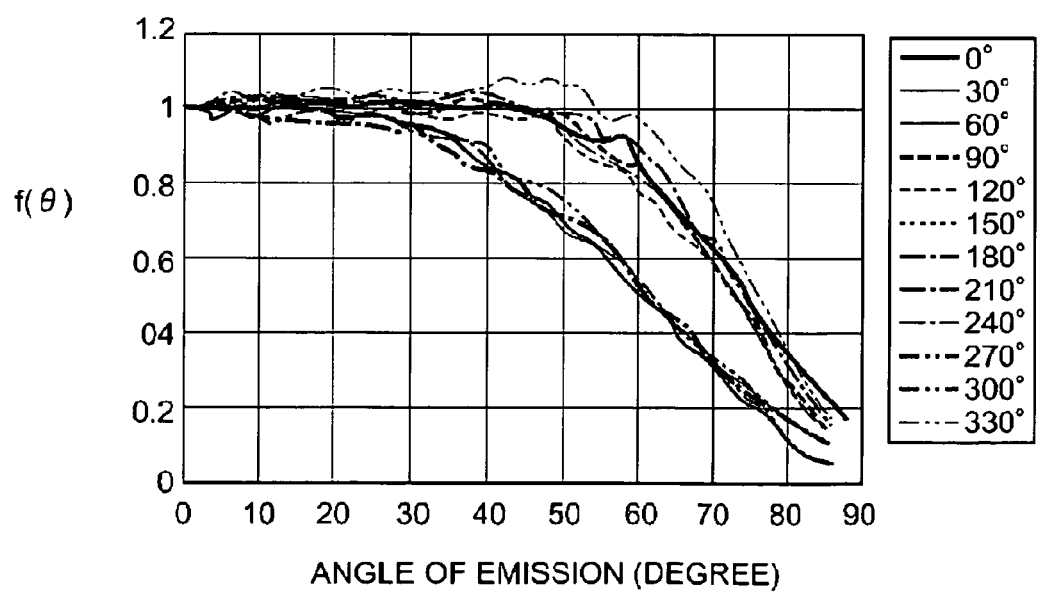
FIG. 20 is a diagram showing spherical light distribution characteristics on the object surface disposed at a distance of 10 mm from the distal end surface of the endoscope at a time when each of the oblique angles εa, εb, εc of three illumination optical systems is set to 15° in the endoscope optical system having the light distribution characteristics shown in FIG. 17.

FIGS. 19 and 20 are graphs showing spherical light distribution characteristics on each object surface in the case where each of oblique angles εa, εb, εc of the three illumination optical systems is set to 15°, and the spherical object is disposed at distances of 40 mm and 10 mm from the distal end surface of the spherical object. When the illumination optical systems are oblique, as shown in FIGS. 19, 20, it is possible to achieve an illumination system in which the light distribution characteristics are well balanced and which does not have any illuminance unevenness.

There is another advantage in directing the illumination optical system outwardly. That is, in the case where an illumination system whose illuminance gradually drops away from the visual field center is used in the endoscope optical system, when the distal end surface of the endoscope is flat (oblique angle of 0°), the illuminance is excessively high in the center of the visual field. Depending on the object, there is a fear that a phenomenon (halation) occurs in which the object cannot be observed due to an excessively high luminance in the center of the visual field. When the illumination optical system is slightly oblique, and the high illuminance is dispersed as in Embodiment 3, the light distribution balance becomes better.

Additionally, when the oblique angle of the illumination optical system is set to be larger than 20°, the light distribution balance at a time when the distance from the distal end surface of the endoscope to the object surface is set to 10 mm is improved. On the other hand, it is difficult to make a light guide fiber bundle oblique and assemble it into the illumination optical system. The outer diameter of the distal end portion of the endoscope increases. In addition to the above-described demerits in production and specifications, there is a possibility of a disadvantage in that the visual field center darkens, when the distal end of the endoscope comes closer to the object.

Embodiment 4

Figure 21:
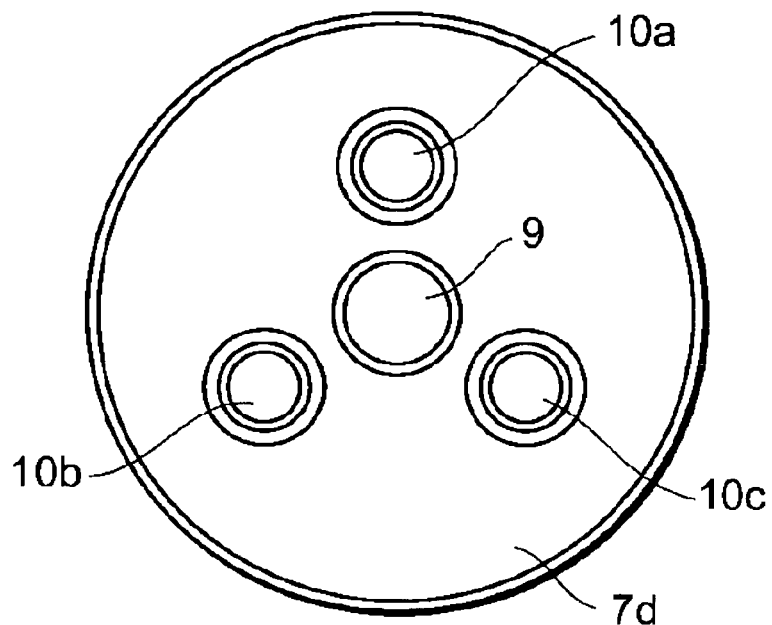
FIG. 21 is a diagram showing a layout of an optical system in the distal end portion of the endoscope as viewed from an object side according to Embodiment 4 of the present invention.

FIG. 21 is an explanatory view showing the layout of an endoscope optical system as viewed from the object side according to Embodiment 4 of the present invention.

The endoscope optical system of Embodiment 4 is provided with an observation optical system 9 having a field angle of 160°, and three illumination optical systems 10a, 10b, and 10c. The distal end surface 7d of the endoscope is formed into a substantially flat surface. As viewed from the front (object side), the three illumination optical systems 10a, 10b and 10c are arranged in such a manner as to surround the observation optical system 9. Each of the three illumination optical systems 10a, 10b and 10c comprise one positive lens as shown in FIG. 7. The systems satisfy the conditions (1) and (2), and are appropriate as those for combined use with an observation optical system having a large angle of field.

Moreover, as shown in FIG. 21, the three illumination optical systems 10a, 10b and 10c are arranged in such a manner that the center of the lens closest to the object side of the observation optical system 9 is positioned in the area of a triangle made by mutually connecting centers of lenses closest to the object sides of the three illumination optical systems 10a, 10b and 10c.

Furthermore, assuming that the direction of a straight line connecting the center of the lens closest to the object side of the observation optical system 9 to that of the lens closest to the object side of the illumination optical system 10a is 0°, angles φ1, φ2 in directions connecting the center of the lens closest to the object side of the observation optical system 9 to the centers of the lenses closest to the object sides of the illumination optical systems 10b, 10c are 120° and 240°, respectively. Distances ra, rb and rc from the center of the lens closest to the object side of the observation optical system 9 to the centers of the lenses closest to the object sides of the illumination optical systems 10a, 10b, and 10c are 4.5 mm, 4.7 mm, and 5 mm, respectively. The outer diameter of the lens closest to the object side of the observation optical system 9 is 2.3 mm.

In Embodiment 4, since the three illumination optical systems 10a, 10b and 10c are arranged with respect to the observation optical system 9 as described above, it is possible to secure a well-balanced light distribution performance even in a case where the distal end surface of the endoscope comes close to an object surface.

Figure 22:
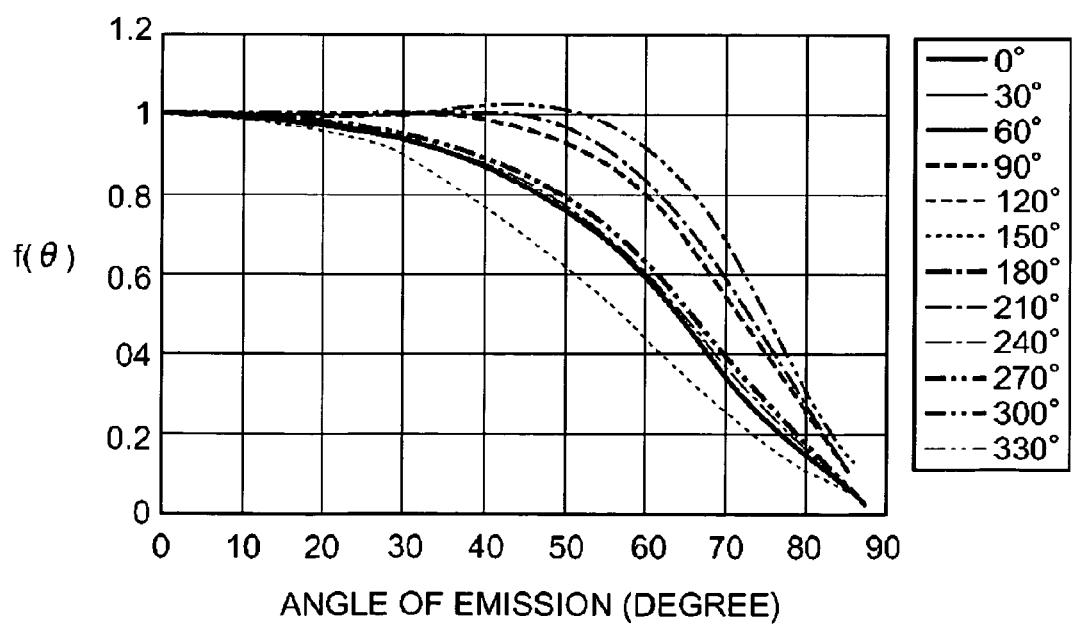
FIG. 22 is a diagram showing light distribution characteristics for each direction in the visual field at the time when the spherical object disposed at a distance of 40 mm from the distal end surface of the endoscope is illuminated by three illumination optical systems 10a, 10b and 10c in Embodiment 4.
Figure 23:
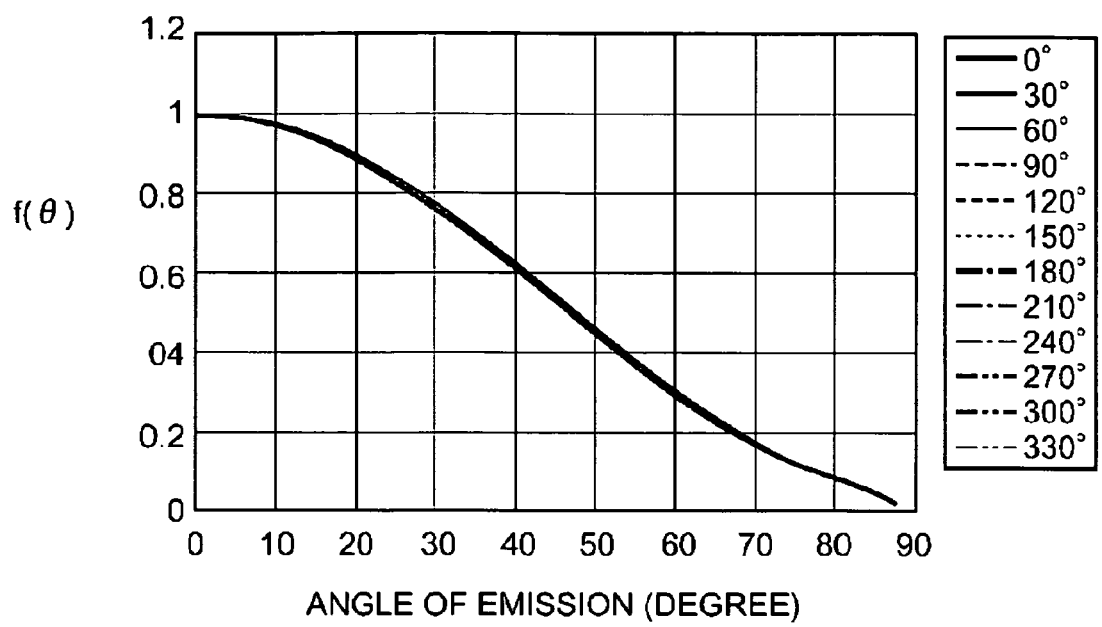
FIG. 23 is a diagram showing light distribution characteristics for each direction in the visual field at the time when the spherical object disposed at a distance of 10 mm from the distal end surface of the endoscope is illuminated by three illumination optical systems 10a, 10b and 10c in Embodiment 4.

FIG. 22 is a graph showing light distribution characteristics on the object surface at a time when a spherical object disposed at a distance of 40 mm from the distal end surface of the endoscope is illuminated simultaneously by the three illumination optical systems 10a, 10b and 10c. FIG. 23 is a graph showing light distribution characteristics on the object surface at a time when the spherical object disposed at a distance of 10 mm from the distal end surface of the endoscope is illuminated simultaneously by the three illumination optical systems 10a, 10b and 10c. In these figures, the meanings of numerical values such as 0° and 30° described on the right outside of frame of the figure are similar to those described with reference to FIG. 17. The origin (reference point of the angle of field) is the center of the distal end surface of the observation optical system 9.

Embodiment 5

Figure 39:
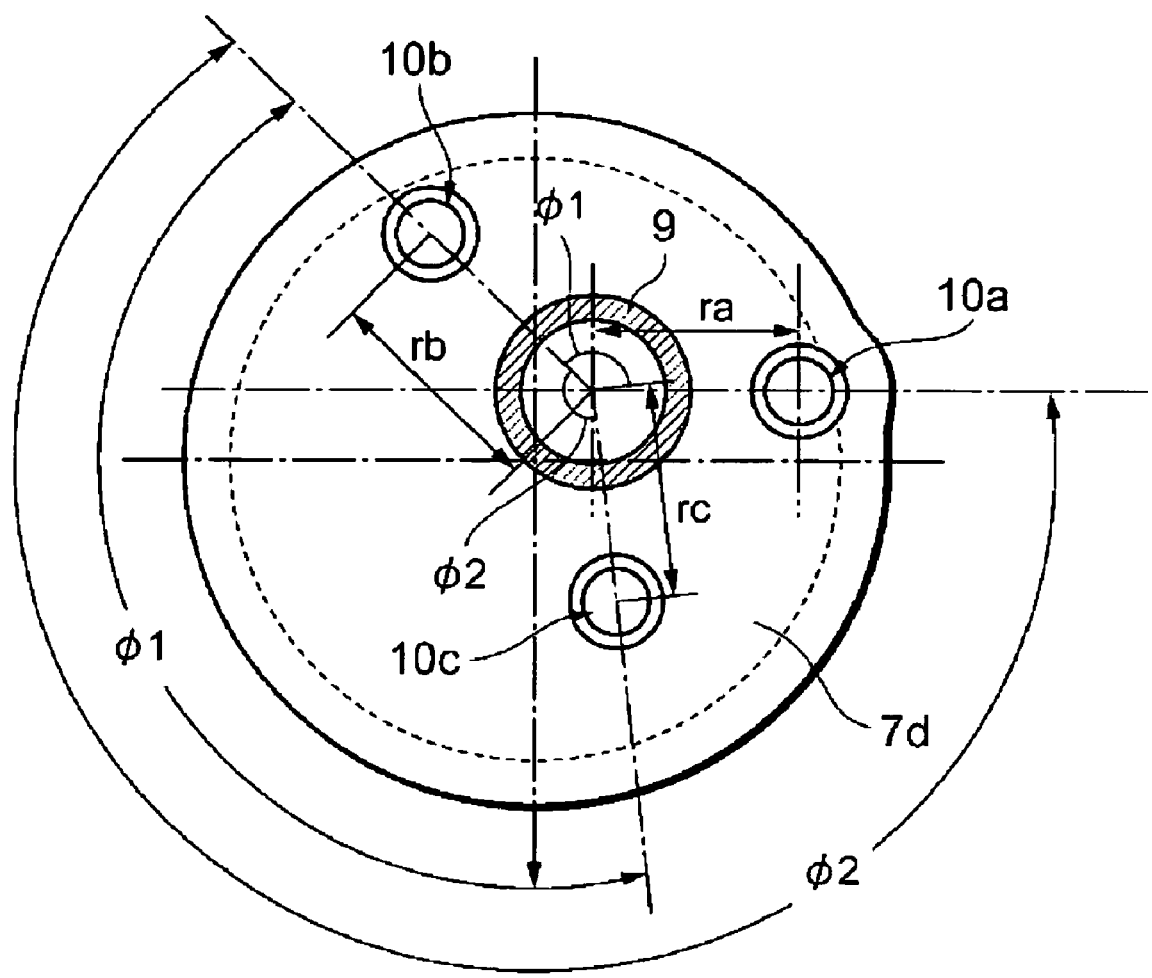
FIG. 39 is an explanatory view showing a layout of the endoscope optical system as viewed from the object side according to Embodiment 5 of the present invention.

FIG. 39 is an explanatory view of a layout of an optical system in a distal end portion of an endoscope as viewed from the object side according to Embodiment 5 of the present invention.

The endoscope optical system of Embodiment 5 is provided with an observation optical system 9 having a field angle of 170°, and three illumination optical systems 10a, 10b and 10c. The distal end surface 7d of the endoscope is formed into a bullet shape in which the observation optical system is at the vertex. As viewed from the front (object side), the three illumination optical systems 10a, 10b and 10c are arranged in such a manner as to surround the observation optical system 9. The three illumination optical systems 10a, 10b and 10c are oblique in such a manner as to direct emissions thereof outwardly with respect to an optical axis of the observation optical system in accordance with the bullet shape of the distal end surface 7d. Oblique angles εa, εb and εc of the three illumination optical systems 10a, 10b and 10c are 8°, 8° and 0°. Each of the three illumination optical systems 10a, 10b and 10c comprises one positive lens as shown in FIG. 7. The systems satisfy the conditions (1) and (2), and are appropriate as those for combined use with an observation optical system having a large angle of field.

Moreover, assuming that the direction of a straight line connecting the center of a lens closest to the object side of the observation optical system 9 to that of the lens closest to the object side of the illumination optical system 10b is 0°, angles φ1, φ2 in directions connecting the center of the lens closest to the object side of the observation optical system 9 to the centers of the lenses closest to the object sides of the illumination optical systems 10c and 10a are 139° and 223°, respectively. Distances ra, rb, and rc from the center of the lens closest to the object side of the observation optical system 9 to the centers of the lenses closest to the object sides of the illumination optical systems 10a, 10b and 10c are 4.04 mm, 4.54 mm and 4.25 mm, respectively. The outer diameter of the lens closest to the object side of the observation optical system 9 is 1.8 mm.

In Embodiment 5, since the three illumination optical systems 10a, 10b and 10c are arranged with respect to the observation optical system 9 as described above, it is possible to secure a well-balanced light distribution performance even in a case where the distal end surface of the endoscope comes close to an object surface.

Figure 40:
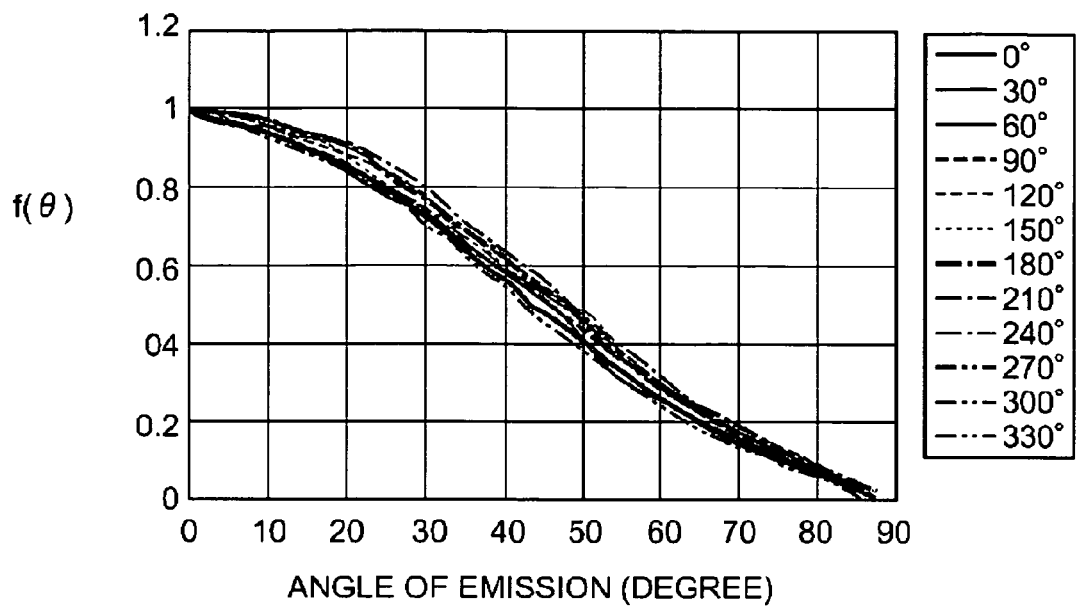
FIG. 40 is a diagram showing light distribution characteristics for each direction in the visual field at a time when the spherical object disposed at a distance of 40 mm from the distal end surface of the endoscope is illuminated in Embodiment 5.
Figure 41:
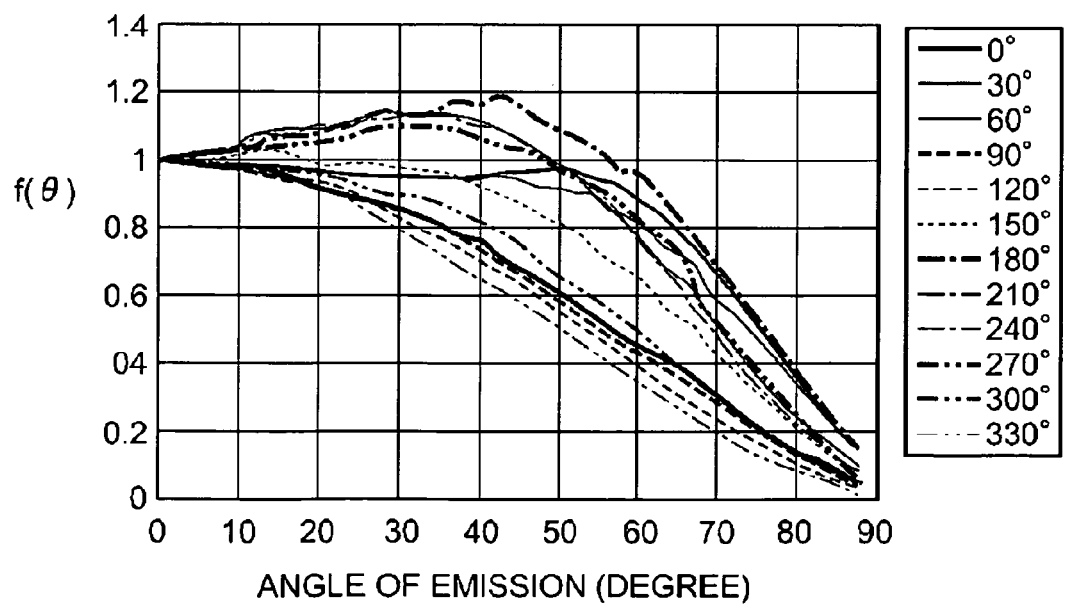
FIG. 41 is a diagram showing light distribution characteristics for each direction in the visual field at a time when the spherical object disposed at a distance of 10 mm from the distal end surface of the endoscope is illuminated in Embodiment 5.

FIG. 40 is a graph showing light distribution characteristics on the object surface at a time when a spherical object disposed at a distance of 40 mm from the distal end surface of the endoscope is illuminated simultaneously by the three illumination optical systems 10a, 10b and 10c. FIG. 41 is a graph showing light distribution characteristics on the object surface at a time when a spherical object disposed at a distance of 10 mm from the distal end surface of the endoscope is illuminated simultaneously by the three illumination optical systems 10a, 10b and 10c. In these figure, meanings of numerical values such as 0° and 30° described on the right outside of the frame of the figure are similar to those described with reference to FIG. 17; The origin (reference point of the angle of field) is a center of the distal end surface of the observation optical system 9.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An optical system for endoscope for use in a distal end portion of an endoscope, comprising:

an observation optical system; and a plurality of illumination optical systems which allow light emitted from a light source to diverge, at least one of the plurality of illumination optical systems satisfying the following condition (1):

$$0 \leq -df(\theta)/d\theta < 0.025, \ 10° \leq \theta \leq 85° \quad (1),$$

wherein θ denotes an angle of emission from a center of the illumination optical system, and f(θ) denotes a spherical light distribution characteristics that is defined by an illuminance distribution at a time when a spherical object is illuminated by the illumination optical system, which is normalized with an illuminance at a time when the angle θ of emission is 0°;

and wherein the illumination optical system satisfying the condition (1) satisfies the following condition (7):

$$0.05 \leq f(80°) \leq 0.15 \quad (7),$$

wherein f(80°) is a value of f(θ) at a time when the angle θ of emission is 80°.

2. The optical system for an endoscope according to claim 1, wherein the at least one illumination optical system satisfies the following condition (2):

$$0 \leq -df(\theta)/d\theta < 0.02, \ 65° \leq \theta \leq 80° \quad (2).$$

3. An optical system for endoscope for use in a distal end portion of an endoscope, comprising:

an observation optical system; and three illumination optical systems which allow light emitted from a light source to diverge, at least one of the illumination optical systems satisfying the following condition (1):

$$0 \leq -df(\theta)/d\theta \leq 0.025, 10° \leq \theta \leq 85° \quad (1),$$

wherein θ denotes an angle of emission from a center of the illumination optical system, and f(θ) denotes a spherical light distribution characteristics that is defined by an illuminance distribution at a time when a spherical object is illuminated by the illumination optical system, which is normalized with an illuminance at a time when the angle θ of emission is 0°, wherein when the three illumination optical systems are arranged in such a manner that a center of a lens closest to an object side of the observation optical system is positioned in an area of a triangle made by mutually connecting centers of lenses closest to the object sides of the three illumination optical systems, and assuming that a direction of a straight line connecting the center of the lens closest to the object side of the observation optical system to that of the lens closest to the object side of one of the illumination optical systems is 0°, and angles in directions of straight lines connecting the center of the lens closest to the object side of the observation optical system to the centers of the lenses closest to the object sides of the other two illumination optical systems are $\phi 1$, $\phi 2$, respectively, the following conditions (3) and (4) are satisfied, and assuming that a distance from the center of the lens closest to the object side of the observation optical system to that of the lens closest to the object side of each illumination optical system is r, the following condition (5) is satisfied:

$$95° \leq \phi 1 \leq 145° \quad (3);$$

$$215° \leq \phi 2 \leq 265° \quad (4); \text{ and}$$

$$1.3 \leq r/d \leq 3 \quad (5),$$

wherein d denotes an outer diameter of the lens closest to the object side in the observation optical system.

4. The optical system for an endoscope according to claim 3, wherein:

when a distal end surface of a distal end portion of the endoscope is formed into a bullet shape in which the observation optical system is at its vertex, at least two of the plurality of illumination optical systems are obliquely disposed in such a manner that emission surfaces thereof are directed outwardly with respect to an optical axis of the observation optical system, and assuming that an angle formed by the optical axis of the observation optical system and that of each illumination optical system disposed in such a manner that the emission surface is outwardly directed is ϵ, the following condition (6) is satisfied:

$$5° \leq \epsilon \leq 20° \quad (6).$$

5. The optical system for an endoscope according to claim 3, wherein:

when a distal end surface of a distal end portion of the endoscope is formed into a bullet shape in which the observation optical system is at its vertex, at least two of the plurality of illumination optical systems are obliquely disposed in such a manner that emission surfaces are directed outwardly with respect to an optical axis of the observation optical system, and assuming that an angle formed by the optical axis of the observation optical system and that of each illumination optical system disposed in such a manner that the emission surface is outwardly directed is ϵ, the following condition (6) is satisfied:

$$5° \leq \epsilon \leq 20° \quad (6).$$

6. The optical system for an endoscope according to claim 1, wherein, in the illumination optical system, at least one surface comprises a roughened surface.

7. The optical system for endoscope according to claim 6, wherein, in the illumination optical system, the spherical light distribution characteristics f(θ) satisfy the following condition (8), and the angle θ of emission satisfying the following condition (9) exists in a range of 60° to 70°:

$$-df(\theta)/d\theta \leq 0.015, 0° \leq \theta \leq 40° \quad (8); \text{ and}$$

$$f(\theta) = 0.02 \quad (9).$$

8. The optical system for an endoscope according to claim 6, wherein the illumination optical system satisfying the condition (7) comprises only one piano-convex lens having a positive power and having a convex surface of an aspherical surface shape provided with a roughened surface.

* * * * *

UNITED STATES PATENT AND TRADEMARK OFFICE
CERTIFICATE OF CORRECTION

PATENT NO. : 7,585,274 B2 Page 1 of 1
APPLICATION NO. : 11/213905
DATED : September 8, 2009
INVENTOR(S) : Hiroyuki Homma It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 993 days.

Signed and Sealed this

Fourteenth Day of December, 2010

David J. Kappos
*Director of the United States Patent and Trademark Office*